(12) United States Patent
Gao et al.

(10) Patent No.: US 11,873,374 B2
(45) Date of Patent: Jan. 16, 2024

(54) SWELLABLE AND STRUCTURALLY HOMOGENOUS HYDROGELS AND METHODS OF USE THEREOF

(71) Applicant: Massachusetts Institute of Technology, Cambridge, MA (US)

(72) Inventors: Ruixuan Gao, Cambridge, MA (US); Linyi Gao, Cambridge, MA (US); Chih-Chieh Yu, Cambridge, MA (US); Edward Stuart Boyden, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1303 days.

(21) Appl. No.: 16/267,849

(22) Filed: Feb. 5, 2019

(65) Prior Publication Data
US 2019/0256633 A1 Aug. 22, 2019

Related U.S. Application Data

(60) Provisional application No. 62/626,920, filed on Feb. 6, 2018.

(51) Int. Cl.
*C08J 3/075* (2006.01)
*C08G 65/26* (2006.01)
(Continued)

(52) U.S. Cl.
CPC ............ *C08J 3/075* (2013.01); *C08F 8/00* (2013.01); *C08F 8/12* (2013.01); *C08F 8/30* (2013.01);
(Continued)

(58) Field of Classification Search
CPC ...... C08J 3/075; C08J 3/246; C08J 2400/206; C08J 2300/206; C08G 65/32; C08G 65/2624; C08G 81/025; C08G 2210/00; C12Q 1/6834; C12Q 1/6841; C12Q 1/68; C12Q 1/6869; C12Q 2523/101; C12Q 2521/107; C12Q 2525/191;
(Continued)

(56) References Cited

U.S. PATENT DOCUMENTS 5,952,232 A 9/1999 Rothman
6,107,081 A 8/2000 Feeback et al.
(Continued)

FOREIGN PATENT DOCUMENTS

CN 104350372 A 2/2015
EP 3159361 A1 4/2017
(Continued)

OTHER PUBLICATIONS

Zhou et al. "Synthesis and characterization of well-defined PAA-PEG multi-responsive hydrogels by ATRP and click chemistry", RSC Adv., 2014, 4, 54631-54640 (Year: 2014).*
(Continued)

*Primary Examiner* — Michael M. Bernshteyn
(74) *Attorney, Agent, or Firm* — Pierce Atwood LLP

(57) ABSTRACT

The invention encompasses hydrogels, monomer precursors of the hydrogels, methods for the preparation thereof, and methods of use therefor. The linking of monomers can take place using non-radical, bioorthogonal reactions such as copper-free click-chemistry.

11 Claims, 13 Drawing Sheets
Specification includes a Sequence Listing.

(51) Int. Cl.

| | | |
|---|---|---|
| *C12Q 1/6834* | (2018.01) | |
| *C12Q 1/6841* | (2018.01) | |
| *G01N 33/545* | (2006.01) | |
| *C08G 81/02* | (2006.01) | |
| *C08F 8/12* | (2006.01) | |
| *G01N 1/30* | (2006.01) | |
| *C08J 3/24* | (2006.01) | |
| *C12Q 1/68* | (2018.01) | |
| *C08F 8/30* | (2006.01) | |
| *C08G 65/32* | (2006.01) | |
| *C12Q 1/6869* | (2018.01) | |
| *C08F 8/44* | (2006.01) | |
| *C08F 8/00* | (2006.01) | |
| *C08F 222/10* | (2006.01) | |
| *C08F 220/04* | (2006.01) | |
| *G01N 15/02* | (2006.01) | |
| *G01N 1/36* | (2006.01) | |
| *C08F 220/30* | (2006.01) | |
| *C08F 220/34* | (2006.01) | |

(52) U.S. Cl.
CPC .......... *C08F 8/44* (2013.01); *C08F 222/104* (2020.02); *C08G 65/2624* (2013.01); *C08G 65/32* (2013.01); *C08G 81/025* (2013.01); *C08J 3/246* (2013.01); *C12Q 1/68* (2013.01); *C12Q 1/6834* (2013.01); *C12Q 1/6841* (2013.01); *C12Q 1/6869* (2013.01); *G01N 1/30* (2013.01); *G01N 33/545* (2013.01); *C08F 220/04* (2013.01); *C08F 220/303* (2020.02); *C08F 220/346* (2020.02); *C08F 2438/01* (2013.01); *C08G 2210/00* (2013.01); *C08J 2300/206* (2013.01); *C08J 2400/206* (2013.01); *C12Q 2523/101* (2013.01); *G01N 1/36* (2013.01); *G01N 15/0205* (2013.01)

(58) Field of Classification Search
CPC ........ C12Q 2527/125; C12Q 2543/101; G01N 33/545; G01N 1/30; G01N 1/36; G01N 15/0205; C08F 8/12; C08F 8/30; C08F 8/44; C08F 8/00; C08F 222/104; C08F 220/303; C08F 220/346; C08F 20/18; C08F 8/04
USPC ........................................................ 526/321
See application file for complete search history.

(56) References Cited

U.S. PATENT DOCUMENTS

| | | | |
|---|---|---|---|
| 6,204,064 B1 | 3/2001 | Alberts et al. | |
| 6,271,278 B1 | 8/2001 | Park et al. | |
| 6,287,870 B1 | 9/2001 | Wardlaw | |
| 10,059,990 B2 * | 8/2018 | Boyden ................ | C12Q 1/6874 |
| 10,309,879 B2 | 6/2019 | Chen et al. | |
| 10,317,321 B2 | 6/2019 | Tillberg et al. | |
| 10,364,457 B2 | 7/2019 | Wassie et al. | |
| 10,526,649 B2 | 1/2020 | Chen et al. | |
| 10,563,257 B2 | 2/2020 | Boyden et al. | |
| 10,774,367 B2 | 9/2020 | Fraser et al. | |
| 10,995,361 B2 | 5/2021 | Chen et al. | |
| 11,180,804 B2 | 11/2021 | Chen et al. | |
| 11,408,890 B2 | 8/2022 | Boyden et al. | |
| 2002/0176880 A1 | 11/2002 | Cruise et al. | |
| 2003/0120231 A1 | 6/2003 | Wang et al. | |
| 2004/0115629 A1 | 6/2004 | Panzer et al. | |
| 2004/0137527 A1 | 7/2004 | Sleytr et al. | |
| 2004/0248326 A1 | 12/2004 | Ziaie et al. | |
| 2005/0034990 A1 | 2/2005 | Crooks et al. | |
| 2005/0069877 A1 | 3/2005 | Gandhi et al. | |
| 2005/0090016 A1 | 4/2005 | Rich et al. | |
| 2005/0169962 A1 | 8/2005 | Bhatia et al. | |
| 2005/0196702 A1 | 9/2005 | Bryant et al. | |
| 2006/0000767 A1 | 1/2006 | Trauger et al. | |
| 2006/0003356 A1 | 1/2006 | Shaw et al. | |
| 2006/0110760 A1 | 5/2006 | Kim et al. | |
| 2006/0115146 A1 | 6/2006 | Ogura et al. | |
| 2006/0165912 A1 | 7/2006 | Koberstein et al. | |
| 2007/0023942 A1 | 2/2007 | Andino et al. | |
| 2007/0026432 A1 | 2/2007 | Ke et al. | |
| 2007/0042954 A1 | 2/2007 | Chen et al. | |
| 2007/0134902 A1 | 6/2007 | Bertino et al. | |
| 2007/0177786 A1 | 8/2007 | Bartels | |
| 2008/0139407 A1 | 6/2008 | Slootstra et al. | |
| 2008/0261834 A1 | 10/2008 | Simon | |
| 2008/0286360 A1 | 11/2008 | Shoichet | |
| 2009/0011141 A1 | 1/2009 | Carter et al. | |
| 2009/0011420 A1 | 1/2009 | Barron et al. | |
| 2009/0096133 A1 | 4/2009 | Doyle et al. | |
| 2009/0191627 A1 | 7/2009 | Fadeev et al. | |
| 2009/0241681 A1 | 10/2009 | Machauf et al. | |
| 2010/0041128 A1 | 2/2010 | Banes et al. | |
| 2010/0055161 A1 | 3/2010 | Ahn | |
| 2010/0056445 A1 | 3/2010 | Sharma et al. | |
| 2010/0068725 A1 | 3/2010 | Armbruster et al. | |
| 2010/0096334 A1 | 4/2010 | Edmiston | |
| 2010/0111396 A1 | 5/2010 | Boucheron | |
| 2010/0119755 A1 | 5/2010 | Chung et al. | |
| 2010/0248977 A1 | 9/2010 | Johnston et al. | |
| 2011/0009171 A1 | 1/2011 | Watanabe et al. | |
| 2011/0070604 A1 | 3/2011 | Gimzewski et al. | |
| 2011/0087315 A1 | 4/2011 | Richardson-Burns et al. | |
| 2011/0091717 A1 | 4/2011 | Weiss | |
| 2011/0091922 A1 | 4/2011 | Krishnan et al. | |
| 2011/0291357 A1 | 12/2011 | Boyle | |
| 2012/0025271 A1 | 2/2012 | Nakano | |
| 2012/0184670 A1 | 7/2012 | Kobayashi et al. | |
| 2012/0220478 A1 | 8/2012 | Shaffer | |
| 2012/0251527 A1 | 10/2012 | Reiser | |
| 2012/0310223 A1 | 12/2012 | Knox et al. | |
| 2013/0045503 A1 | 2/2013 | Miyawaki et al. | |
| 2013/0203605 A1 | 8/2013 | Shendure et al. | |
| 2014/0087139 A1 | 3/2014 | Rowley et al. | |
| 2014/0193651 A1 | 7/2014 | Kharlampieva et al. | |
| 2014/0364330 A1 | 12/2014 | Mershin et al. | |
| 2015/0086103 A1 | 3/2015 | Tsunomori | |
| 2015/0087001 A1 | 3/2015 | Gradinaru et al. | |
| 2015/0226743 A1 | 8/2015 | Weiss et al. | |
| 2015/0353989 A1 | 12/2015 | Fraser et al. | |
| 2015/0370961 A1 | 12/2015 | Zhang et al. | |
| 2015/0376261 A1 | 12/2015 | Steyaert et al. | |
| 2016/0116384 A1 | 4/2016 | Chen et al. | |
| 2016/0252528 A1 | 9/2016 | Sangaralingham et al. | |
| 2016/0265046 A1 | 9/2016 | Zhang et al. | |
| 2016/0304952 A1 * | 10/2016 | Boyden ................ | C12Q 1/6874 |
| 2016/0305856 A1 | 10/2016 | Boyden et al. | |
| 2017/0067096 A1 | 3/2017 | Wassie et al. | |
| 2017/0081489 A1 | 3/2017 | Rodriques et al. | |
| 2017/0087489 A1 | 3/2017 | Terlingen et al. | |
| 2017/0089811 A1 | 3/2017 | Tillberg et al. | |
| 2017/0103521 A1 | 4/2017 | Chukka et al. | |
| 2017/0182220 A1 | 6/2017 | Song et al. | |
| 2017/0199104 A1 | 7/2017 | Gradinaru et al. | |
| 2017/0276598 A1 | 9/2017 | Ikuyama | |
| 2017/0323431 A1 | 11/2017 | Sarkar et al. | |
| 2018/0119219 A1 | 5/2018 | Chen et al. | |
| 2019/0064037 A1 | 2/2019 | Boyden et al. | |
| 2019/0071656 A1 | 3/2019 | Chang et al. | |
| 2019/0113423 A1 | 4/2019 | Goodman et al. | |
| 2020/0041514 A1 | 2/2020 | Boyden et al. | |
| 2020/0049599 A1 | 2/2020 | Alexander et al. | |
| 2020/0081005 A1 | 3/2020 | Boyden et al. | |
| 2020/0217853 A1 | 7/2020 | Estandian et al. | |
| 2020/0271556 A1 | 8/2020 | Sarkar et al. | |
| 2021/0130882 A1 | 5/2021 | Boyden et al. | |

(56) References Cited

U.S. PATENT DOCUMENTS

| | | |
|---|---|---|
| 2021/0190652 A1 | 6/2021 | Quevedo et al. |
| 2021/0196856 A1 | 7/2021 | Boyden et al. |

FOREIGN PATENT DOCUMENTS

| | | |
|---|---|---|
| JP | 2005291759 A1 | 10/2005 |
| JP | 2006036957 A | 2/2006 |
| JP | 2008286694 A | 11/2008 |
| JP | 2009191125 A | 8/2009 |
| JP | 2014005231 | 1/2014 |
| WO | 2000008212 A1 | 2/2000 |
| WO | 2007103665 A2 | 9/2007 |
| WO | 2008058302 A1 | 6/2008 |
| WO | 2010048605 A1 | 4/2010 |
| WO | 2012142664 A1 | 10/2012 |
| WO | 2014025392 A1 | 2/2014 |
| WO | 2014152984 A1 | 9/2014 |
| WO | 2015041755 A1 | 3/2015 |
| WO | 2015127183 A2 | 8/2015 |
| WO | 2016040489 A1 | 3/2016 |
| WO | 2017027367 A1 | 2/2017 |
| WO | 2017027368 A1 | 2/2017 |
| WO | 2017031249 | 2/2017 |
| WO | 2017079406 A1 | 5/2017 |
| WO | 2017147435 A1 | 8/2017 |
| WO | 2018157074 A1 | 8/2018 |
| WO | 2019144391 A1 | 8/2019 |
| WO | 2021051011 A1 | 3/2021 |

OTHER PUBLICATIONS

Olga et al. "Introduction of anti-fouling coatings at the surface of supramolecular elastomeric materials via post-modification of reactive supramolecular additives", J. Polym. Chem., 2017, 8, 5228-5238 (Year: 2017).*

Hu et al. "Bioorthogonally Cross-Linked Hydrogel Network with Precisely Controlled Disintegration Time over a Broad Range", J. Am. Chem. Soc. 2014, 136, 4105-4108 (Year: 2014).*

Al, H. et al., "Exploration of new chromophore structures leads to the identification of improved blue fluorescent proteins," Biochemistry, 46, 2007, 5904-10.

Akhavan, A. et al., "Molecular Epizootiology of Rodent Leishmaniasis in a Hyperendemic Area of Iran," Iranian J Publ. Health, vol. 39, No. 1, 2010, 1-7.

Asano, S. M. et al., Expansion Microscopy: Protocols for Imaging Proteins and RNA in Cells and Tissues, Current Protocols in Cell Bio., vol. 80, No. 1, Online: DOI: 10.1002/cpcb.56. Retrieved from the Internet: URL:https://onlinelibrary.wiley.com/doi/fullxml/10.1002/cpcb.56> [retrieved on Feb. 26, 2021], Sep. 2, 2018.

Bates, M. et al., "Multicolor super-resolution imaging with photoswitchable fluorescent probes," Science, 317, 2007, 1749-1753.

Batish, M. et al., "Neuronal mRNAs Travel Singly into Dendrites," PNAS, vol. 109(12), 012, 4645-4650.

Beliveau, B. et al., "Versatile design and synthesis platform for visualizing genomes with Oligopaint FISH probes," PNAS, vol. 109(52): pfa, 2012, 21301-21306.

Bleckmann, J. et al., "Surface-Layer Lattices as Patterning Element for Multimeric Extremozymes," Small Journal, 2013, 1-8.

Bokman, S. H. et al. "Renaturation of Aequorea green-fluorescent protein." Biochem. Biophys. Res. Commun. 101, 1372-80 (1981).

Bossi, M. et al. "Multicolor far-field fluorescence nanoscopy through isolated detection of distinct molecular species." Nano Lett. 8, 2463-8 (2008).

Boutin, J. A. "Myristoylation." Cell. Signal, 9(1):15-35. (Jan. 1997) doi: 10.1016/S0898-6568(96)00100-3.

Breitwieser, A. et al., "Magnetic Beads Functionalized with Recombinant S-Layer Protein Exhibit High Human IgG-Binding and Anti-Fouling Properties," Current Topics in Peptide & Protein Research, vol. 17, 2016, 45-55.

Bruchez, M. et al., "Semiconductor nanocrystals as fluorescent biological labels." Science, vol. 281, 1998, Jun. 2013.

Buckley, P. et al., "Cytoplasmic Intron Sequence-Retaining Transcripts Can Be Dendritically Targeted via ID Element Retrotransposons," Neuron, vol. 69, 2011, 877-884.

Buenrostro, J. D. et al., AT AC-seq: A Method for Assaying Chromatin Accessibility Genome-Wide in 'Current Protocols in Molecular Biology,' Wiley, New York, NY, Jan. 5, 2015.

Bullock, G. R. "The current status of fixation for electron microscopy: A review." J. Microsc., 133: 1-15. (1984). doi:10.1111/j.1365-2818.1984.tb00458.x.

Buxbaum, A. et al., "Single-Actin mRNA Detection in Neurons Reveals a Mechanism for Regulating Its Translatability," Science, vol. 343, 2014, 419-422.

Cabili, M. et al., "Localization and abundance analysis of human lncRNAs at single-cell and single-molecule resolution," Genome Biology, vol. 16(20), 2015.

Cai. D., et al. "Improved tools for the Brainbow toolbox." Nat. Methods 10, 540-7 (2013).

Cajigas, I. et al., "The local transcriptome in the synaptic neuropil revealed by deep sequencing and high-resolution imaging," Neuron 74, 2012, 453-466.

Cao, W.,"DNA ligases and ligase-based technologies," Clinical and Applied Immunology Reviews, Elsevier, Amsterdam, NL, vol. 2, No. 1, Jan. 15, 2001, 33-43.

Carpenter, A. E. et al., "CellProfiler: image analysis software for identifying and quantifying cell phenotypes," Genome Biol., 7, 2006, R100.

Chen, F. et al., "Supplementary Material for Expansion Microscopy", Science, 34 7(6221 ), Jan. 15, 2015, 543-548.

Chen, K. et al., "Spatially resolved, highly multiplexed RNA profiling in single cells," Science. vol. 348(6233), 2015, aaa6090-aaa6090.

Chen, X et al. "AT AC-see reveals the accessible genome by transposase-mediated imaging and sequencing," Nature Methods, vol. 13, No. 12, Oct. 17, 2016, 1813-1828.

Chen, X et al. [Supplementary material] "AT AC-see reveals the accessible genome by transposase-mediated imaging and sequencing." Nature Methods, vol. 13, No. 12, Oct. 17, 2016, 1813-1828.

Choi, H. et al., "Next-Generation in Situ Hybridization Chain Reaction: Higher Gain, Lower Cost, Greater Durability." ACS Nano 8(5), 2014, 4284-4294.

Choi, H. et al., "Programmable in situ amplification for multiplexed imaging of mRNA expression," Nature Biotechnology, 28(11), 2010, 1208-1212.

Chozinski, T. et al., "Expansion microscopy with conventional antibodies and fluorescent proteins," Nature Methods, vol. 13(6), 2016, 485-491.

Chu, J. et al., "Non-invasive intravital imaging of cellular differentiation with a bright redexcitable fluorescent protein," Nat. Methods, 11, 2014, 572-8.

Clemson, C. et al., "An architectural role for a nuclear noncoding RNA: NEAT1 RNA is Essential for the Structure of Paraspeckles" Mol Cell. Mar. 27, 2009:33(6):717-26. doi: 10.1016/j.molcel.2009.01.026.

Cochilla, A. J. et al. "Monitoring secretory membrane with FM1-43 flourescence." Annu. Rev. Neurosci. 22:1-10 (1999). doi: 10.1146/annurev.neuro.22.1.1.

Cormack, B. P. et al., "FACS-optimized mutants of the green fluorescent protein (GFP)," Gene, 173, 1996, 33-8.

Cubitt. A. B. et al., "Understanding structure-function relationships in the Aequorea victoria green fluorescent protein," Methods Cell Biol., 58, 1999, 19-30.

Danilozyk, U. G., et al. "Functional relationship between calreticulin, calnexin, and the endoplasmic reticulum luminal domain of calnexin." J. Biol. Chem. 275(17): 13089-13097 (2000). doi:10.1074/jbc.275.17.13089.

Dedecker, P. et al., "Localizer: fast, accurate, open-source, and modular software package for superresolution microscopy," J. Biomed. Opt., 17, 2012, 126008.

(56) References Cited

OTHER PUBLICATIONS

Duan, C. et al., "Application of antigen retrieval method in hMAM immunohistochemical staining of old paraffin- embedded specimens," Academy of Military Medical Sciences, vol. 38(12), Dec. 31, 2014, 965-967.
Edelstein, A. et al., "Computer control of microscopes using µManager," Curr. Protoc. Mol. Biol. Chapter 14, Unit 14.20, 2010.
English, A. R. et al. "Endoplasmic reticulum structure and interconnections with other organelles." Cold Spring Harbor Perspectives in Biology 2013;5:a013227. doi:10.1101/cshperspect. a013227.
English, B. P. et al., "A three-camera imaging microscope for high-speed single-molecule tracking and super- resolution imaging in living cells." Proc SPIE Int Soc Opt Eng. Aug. 21, 2015;9550:955008. doi: 10.1117/12.2190246.
Engreitz, J. et al., "The Xist lncRNA exploits three-dimensional genome architecture to spread across the X chromosomne," Science 341, 2013, 1237973.
Femino, A. et al., "Visualization of Single RNA Transcripts in Situ," Science, vol. 280, 1998, 585-590.
Feng, G. et al., "Imaging neuronal subsets in transgenic mice expressing multiple spectral variants of GFP," Neuron, 28, 2000, 41-51.
Ferri A. "Expansion Microscopy: A New Approach to Microscopic Evaluation. (Master's thesis)." 2020 Retrieved from https://scholarcommons.sc.edu/etd/6034.
Filonov, G. S. et al. "Bright and stable near-infrared fluorescent protein for in vivo imaging." Nat. Biotechnol, 29, 757-61 (2011).
Fouz, M. et al., "Bright Fluorescent Nanotags from Bottlebrush Polymers with DNATipped Bristles," ACS Central Science, vol. 1, 2015, 431-438.
Freifeld, L. et al., "Expansion microscopy of zebrafish for neuroscience and developmental biology studies," PNAS (online), Nov. 21, 2017, E10799-E10808.
Goedhardt, J. et al. "Structure-guided evolution of cyan fluorescent proteins towards a quantum yield of 93%." Nat. Commun. 3, 751 (2012).
Griesbeck, et al., "Reducing the environmental sensitivity of yellow fluorescent protein. Mechanism and applications," J. Biol. Chem., 276, 2001, 29188-94.
Guo A. et al. "The Critical Role of Surface Chemistry In Protein Microarrays" in Functional Protein Microarrays in Drug Discovery, edt. Paul Predki, p. 53-71 (CRC press, Boca Raton, 2007).
Guo, H. et al. "An efficient procedure for protein extraction from formalin-fixed, Paraffin-embedded tissues for reverse phase protein arrays." Proteome Sci. 10:56 (2012) doi: 10.1186/1477-5956-10-56.
Parang et al. "Myeloid translocation genes differentially regulate colorectal cancer programs," Oncogene, Jun. 2016. 35, 6341-6349.
Park, Y. N. et al., "Detection of Hepatitis C Virus RNA Using Ligation-Dependent Polymerase Chain Reaction in Formalin-Fixed, Paraffin-Embedded Liver Tissues," Amer. J. of Pathol., vol. 149, No. 5, Nov. 1, 1996, 1485-1491.
Plath, K. et al., "Xist RNA and the mechanism of X chromosome inactivation," Annu. Rev. Genet. 36, 2002, 233-78.
Product information brochure, FLOCRYL TM MBA, SNF Floerger, pp. 1-4, accessed 1744136.
Proteinase K from Tritirachium album, solution, Serva Electrophoresis, Instruction Manual, Cat. No. 33755, 1 page, publicly available prior to Feb. 1, 2017.
Pum, D. et al., "Reassembly of S-Layer Proteins", Nanotechnology, 2014, 1-15.
Raj, A. et al., "Detection of individual endogenous RNA transcripts in situ using multiple singly labeled probes," Methods in Enzymology, vol. 472 (Elsevier Inc.), 2010, 365-386.
Raj, A. et al., "Imaging individual mRNA molecules using multiple singly labeled probes," Nat. Methods 5(10), 2008, 877-879.
Randall, K. J. et al., "A dual-label technique for the immunohistochemical demonstration of T-lymphocyte subsets in formalin-fixed, paraffin-embedded rat lymphoid tissue," Toxicol. Pathol., 36, 2008, 795-804.
Rego, E. H. et al. "Nonlinear structured-illumination microscopy with a photoswitchable protein reveals cellular structures at 50-nm resolution." Proc. Natl. Acad. Sci. U. S. A. 109, E135-43 (2012).
Reinhart-King, C. A. et al., "Dynamics and Mechanics of Endothelial Cell Spreading." Biophysical J, 89(1):, Jul. 1, 2005, 676-689.
Revelo, N. H. et al. "A new probe for super-resolution imaging of membranes elucidates trafficking pathways." J. Cell Biol. 205(4):591-606 (2014). doi:10.1083/jcb.201402066.
Rose, R. et al., "Ocular ascorbate transport and metabolism," A. Comp. Physiol., 100, 1991, 273-85.
Rothbauer, M. et al., "Exploitation of S-Layer Anisotropy: pH-Dependent Nanolayer Orentation for Cellular Micropatterning," Acs NANO, published online, 2013.
Sarrazin, S. et al. "Heparan sulfate proteoglycans." Cold Spring Harb. Perspect. Biol. 2011:3:a004952. doi: 10.1101/cshperspect. a004952.
Schindelin J., et al., "Fiji: an open-source platfonn for biological-image analysis," Nature Methods, vol. 9, pp. 676-682 (2012).
Schnell, U., et al. "Immunolabeling artifacts and the need for live-cell imaging." Nat. Methods 9, 152-158 (2012).
Scicchitano, M. S., et al. "Protein extraction of formalin-fixed, paraffin-embedded tissue enables robust proteomic profiles by mass spectrometry." J. Histochem. Cytochem. 57(9): 849-860 (2009). doi:10. 1369/jhc.2009.953497.
Seifert, U. "Configurations of fluid membranes and vesicles." Adv. Phys. 46(1):13-137 (1997). doi: 10.1080/00018739700101488.
Seneviratne, U., et al., "S-nitrosation of Proteins Relevant to Alzheimer's Disease During Early Stages of Neurodegeneration," PNAS, vol. 113, No. 15, Apr. 12, 2016, 4152-4157.
Shah, S., et al., "Single-Molecule RNA Detection at Depth Via Hybridization Chain Reaction and Tissue Hydrogel Embedding and Clearing," Jun. 24, 2016, published by the Company of Biologists, Ltd., http://dev.biologists.org/lookup/doi/10.1242/dev.138560.
"Shaner, N. C. et al., "'Improved monomeric red, orange and yellow fluorescent proteinsderived from *Discosoma* sp. red fluorescent protein,'" Nat. Biotechnol., 22, 2004, 1567-72."
Shaner. N. C. et al., "Improving the photostability of bright monomeric orange and red fluorescent proteins," Nat. Methods, 5, 2008, 545-51.
Shcherbakova, D. M. , "An orange fluorescent protein with a large Stokes shift for single-excitation multicolor FCCS and FRET imaging," J. Am. Chem. Soc., 134, 2012, 7913-23.
Shcherbo, D. et al. "Far-red fluorescent tags for protein imaging in living tissues." Biochem. J. 418, 567-74 (2009).
Shen, K., et al. "Comparison of different buffers for protein extraction from formalin-fixed and paraffin-embedded tissue specimens." PLoS One 10(11): e0142650 (2015). doi: 10.1371/journal.pone. 0142650.
Shi, S. R., et al. "Antigen retrieval in formalin-fixed, paraffin-embedded tissues: An enhancement method for immunohistochemical staining based on microwave oven heating of tissue sections." J. Histochem. Cytochem. 39 (6):741-8 (1991) doi: 10.1177/39.6. 1709656.
Sleytr, U. et al., "Heterologous Reattachment of Regular Arrays of Glycoproteins on Bacterial Surfaces," Nature, vol. 257, 1975, 400-401.
Sleytr, U. et al., "S-Layers Principles and Applications," FEMS Microbiology Rev., 2014, 1-42.
Sniegowski, J. A. et al., "Maturation efficiency, trypsin sensitivity, and optical properties of Arg96. Glu222, and Gly67 variants of green fluorescent protein," Biochem. Biophys. Res. Commun., 332, 2005, 657-63.
Steward, O. et al., "Compartmentalized synthesis and degradation of proteins in neurons," Neuron, vol. 40, 2003, 347-359.
Steward, O. et al., "Synaptic activation causes the mRNA for the leg Arc to localize selectively near activated postsynaptic sites on dendrites," Neuron, vol. 21, 1998, 741-751.
Strack, R., "Imaging Bigger is Better for Super-Resolution," Nature Methods, 12(13), Mar. 1, 2015, 169.
Subach, et al. "An Enhanced Monomeric Blue Fluorescent Protein with the High Chemical Stability of the Chromophore", PLoS One, 6, 2011, e28674.

(56) References Cited

OTHER PUBLICATIONS

Subach, F. V. et al., "Bright monomeric photoactivatable red fluorescent protein for two color super-resolution sptPALM of live cells," J. Am. Chem. Soc., 132, 2010, 6481-91.
Tanca, A. et al. "Comparability of differential proteomics data generated from paired archival fresh-frozen and formalin-fixed samples by GeLC-MS/MS and spectral counting." J. Proteomics 77:561-676 (2012). doi:10.1016/j.jprot.2012.09.033.
Tanca, A. et al. "Critical comparison of sample preparation strategies for shotgun proteomic analysis of formalin-fixed, paraffin-embedded samples: Insights from liver tissue." Clin. Proteomics 11:28 (2014). doi: 10.1186/1559-0275-11-28.
Testagrossa et al. "Immunohistochemical expression of podocyte markers in the variants of focal segmental glomerulosclerosis." National Dial Transplant 28: 91-98 (2013).
ThermoFisher Scientific, Epitope Recovery Methods for IHC. Nov. 7, 2015, pp. 1-2.
Thevenaz, P., et al., "A pyramid approach to subpixel registration based on intensity," IEEE Trans. Image Process.7, 27-41 (1998).
Valenzuela, J. I. et al. "Diversifying the secretory routes in neurons." Frontiers in Neuroscience 9:358 (2015). doi:10.3389/fnins.2015.00358.
Van Meer, G., et al. "Membrane lipids: Where they are and how they behave." Nature Reviews Molecular Cell Biology 9(2): 112-124 (2008). doi:10.1038/nrm2330.
Van Vliet, et al.,"The Biomechanics Toolbox: Experimental Approaches for Living Cells and Biomolecules," Acta Materialia 51: pp. 5881-5905, Aug. 23, 2003, [online], retrieved from the Internet, Oct. 23, 2015.
Vedaldi, A. et al. "VIfeat: an open and portable library of computer vision algorithms" in MM '10: Proceedings of the 18th ACM international conference on Multimedia, Oct. 2010 p. 1469-1472. https://doi.org/10.1145/1873951.1874249.
Wachter, R. M. et al., "Sensitivity of the yellow variant of green fluorescent protein to halides and nitrate," Curr. Biol., 9, 1999, R628-R629.
Wang, F. et al., "RNAscope: A novel in situ RNA analysis platform for formalin-fixed, paraffin-embedded tissues, Journal of Molecular Diagnostics," vol. 14(1), 2012, 22-29.
Wassie, A. T., et al. "Expansion microscopy: principles and uses in biological research," Nature Methods 16(1): 33-41 (2019). doi: 10.1038/s41592-018-0219-4.
Weber, P. C., et al. "Structural origins of high-affinity biotin binding to streptavidin," Science 243(4887):85-88 (1989). doi:10.1126/science.2911722.
Wen, G. et al. "Evaluation of direct grafting strategies in Expansion Microscopy," BioRxiv preprint Jul. 8, 2019, doi: https://doi.org/10.1101/696039 (Jul. 8, 2019).
Wu. C. et al., "A method for the comprehensive proteomic analysis of membrane proteins," Nat. Biotechnol., 21, 2003, 532-8.
Bi, X. et al., "In situ-forming cross-linking hydrogel systems: chemistry and biomedical applications", In: "Emerging Concepts in Analysis and Applications of Hydrogels", INTECH, Aug. 24, 2016, 131-158.
Goor, Olga J. et al., "Introduction of anti-fouling coatings at the surface of supramolecular elastomeric materials via post-modification of reactive supramolecular additives", Polymer Chem., vol. 8, No. 34, Jan. 1, 2017, 5228-5238.
Jiang, Y. et al., "Click hydrogels, microgels and nanogels: emerging platforms for drug delivery and tissue engineering", Biomaterials, vol. 35, No. 18, Jun. 1, 2014, 4969-4985.
Majcher, M. J. et al., "Hydrogel synthesis and design", In: "Cellulose-Based Superabsorbent Hydrogels", Springer International Publishing, Jan. 1, 2018, 1-41.
Xu, J. et al., "Bioorthogonally cross-linked hydrogel network with precisely controlled disintegration time over a broad ragne", J. Am. Chem.Soc., vol. 136, No. 11, Mar. 19, 2014, 4105-4108.
Zhou, C. et al., "Synthesis and characterization of well-defined PAA-PEG multi-responsive hydrogels by ATRP and click chemistry", RSC ADV., vol. 4, No. 97, Jan. 1, 2014, 54631-54640.

Wurm, C. A. et al. "Nanoscale distribution of mitochondrial import receptor Torn20 is adjusted to cellular conditions and exhibits an inner-oelluhar gradient." Proc. Natl. Acad. Sci. U. S. A, 108(33):13546-13551 (2011). doi:10.1073/pnas.1107553108.
Yan, B. X. et al. "Glycine residues provide flexibility for enzymeenzyrrte active sites." J. Biol. Chem. 272(6): 318.0-4 (1997). doi:10.1074/jbc.272.6.3190.
Yu, C-C et al., "Expansion microscopy of C.elegans," ELIFE, [Online] DOI: 10.7554/elife.46249. Retrieved from the Internet:URL:https://elifesciences.org/articles/46249> [retrieved on Feb. 26, 2021], May 1, 2020, p. 125.
Zhang, D., et al., "Dynamic DNA nanotechnology using strand-displacement reactions," Nature Chemistry, vol. 3, pp. 103-113 (2011).
Zhang, R. et al., "Tools for GPCR Drug Discovery," Acta Pharmacologica Sinica, 33, 2012, 372-384.
Zhao, Y. et al. "Nanoscale imaging of clinical specimens using pathology-optimized expansion microscopy." Nat. Biotechnol. 35(8): 757-764 (2017). doi:10.1038/nbt.3892.
Zimmerman et al., "Adapting the stretched sample method from tissue profiling to imaging," Proteomics, 8, (2008), p. 3809-3815.
Zuiderveld, K. "Contrast Limited Adaptive Histogram Equalization." in Graphics Gems 474-485 (1994). doi:10.1016/b978-0-12-336156-1.50061-6.
Gurskaya, N. G. et al. "Engineering of a monomeric green-to-red photoactivatable fluorescent protein induced by blue light." Nat. Biotechnol. 24, 461-5 (2006).
Gyorvary, E. S. et al., "Self-Assembly and Recrystallization of Bacterial S-Layer Proteins at Silicon Supports Imaged in Real Time by Atomic Force Microscopy," Journal of Microscopy, vol. 212, 2003, 300-306.
Habuchi, S. et al., "mKikGR, a monomeric photoswitchable fluorescent protein," PLoS One, 3, 2008, e3944.
Hackstadt, T. , "Steric hindrance of antibody binding to surface proteins of Coxiella burnetti by phase I lipopolysaccharide," Infect Immun, 56, 1998, 802-807.
Heim, R. et al., "Engineering green fluorescent protein for improved brightness, longer wavelengths and fluorescence resonance energy transfer," Curr. Biol., 6, 1996, 178-82.
Heim, R. et al., "Wavelength mutations and posttranslational autoxidation of green fluorescent protein," Proc. Natl. Acad. Sci. U.S.A., 91, 1994, 12501-4.
Hoffman, T. L. et al., "A Biosensor Assay for Studying Ligand-Membrane Receptor Interactions: Binding of Antibodies and HIV-1 Env to Chemokine Receptors," PNAS, 97(21), 2000, 11215-11220.
Honig, M. G. et al. "DiI and DiO: versatile fluorescent dyes for neuronal labeling and pathway tracing." Trends Neurosci. 12(9):333-341 (1989). doi:10.1016/0166-2236(89)90040-4.
Honig, M. G. et al. "Fluorescent carbocyanine dyes allow living neurons of identified origin to be studied in long-term cultures." J. Cell Biol. 103:171-187 (1986). doi:10.1083/jcb.103.1.171.
Huang, B. et al., "Whole-cell 3D STORM reveals interactions between cellular structures with nanometer-scale resolution," Nat. Methods, 5, 2008, 104 7-1052.
Huisken, J. et al., "Optical Sectioning Deep Inside Live Embryos by Selective Plane Illumination Microscopy" Science Aug. 13, 2004 vol. 305 Iss. 5686, p. 1007-9.
Hunt et al. "High temperature antigen retrieval and loss of nuclear morphology: a comparison of microwave and autoclave techniques," J Clin Pathol 1996;49:767-770.
International Search Report and Written Opinion from the International Searching Authority dated Jul. 19, 2019 from corresponding International Patent Application No. PCT/US2019/016609 Filed on Feb. 5, 2019.
Invitrogen "Crosslinking and Photoactivatable Reagents," Chapter 5 in "Molecular Probes TM Handbook a Guide to Fluorescent Probes and Labeling Technologies", 11th Edition, 2010, 171-188.
Jamur, M. C. et al. "Permeabilization of Cell Membranes." in Immunocytochemical Methods and Protocols 588:63-6 (2010). doi:10.1007/978-1-59745-324-0_9.
Jekel, P A. et al., "Use of endoproteinase Lys-C from Lysobacter enzymogenes in protein sequence analysis," Anal. Biochem., 134, 1983, 347-354.

(56) References Cited

OTHER PUBLICATIONS

Jimenez, N. et al., "A Novel Approach for Intracellular 3D Immuno-Labeling for Electron Tomography," Traffic, 13, 2012, 926-933.
Jung, H. et al., "Axonal mRNA localization and local protein synthesis in nervous system assembly, maintenance and repair," Nat. Rev. Neurosci., vol. 13(5), 2012, 308-24.
Kakimoto, K. et al., "Hypothesis for the mechanism for heat-induced antigen retrieval occurring on fresh frozen sections without formalin-fixation in immunohistochemistry," J Mol Histol., 39, 2008, 389-399.
Kaur, et al., "Thermodynamic, Counterion, and Hydration Effects for the Incorporation of Locked Nucleic Acid Nucleotides into DNA Duplexes" Biochemistry 45, 2006, 7347-7355.
Ke R. et al. "In situ sequencing for RNA analysis in preserved tissue and cells." Nat Methods. Sep. 2013; 10(9):857-60. Epub Jul. 14, 2013.
Ke, R. et al., [Supplementary Material] "In situ sequencing for RNA analysis in preserved tissue and cells," Nature Methods 10(9):857-60, 2013, 1-29.
Kroon, D.J , "B-spline Grid, Image and Point based Registration," Matlab Cent. At <http://www.mathworks.com/matlabcentral/fileexchange/20057-b-spline-grid--image-and-point-based-registration>.
Ku, T. et al. "Multiplexed and scalable super-resolution imaging of three-dimensional protein localization in size-adjustable tissues." Nat. Biotechnol. 34(9): 973-981 (2016). doi:10.1038/nbt.3641.
Laemmli, U. K. "Cleavage of structural proteins during the assembly of the head of bacteriophage T4." Nature 227, 680-685 (1970).
Lakkaraju, A. K. K. et al. "Palmitoylated calnexin is a key component of the ribosome-translocon complex." EMBO J. 31, 1823-1835 (2012). doi:10.1038/emboj.2012.15.
Lam, A. J. et al. "Improving FRET dynamic range with bright green and red fluorescent proteins." Nat. Methods 9, 1005-12 (2012).
Lee et al. "Highly multiplexed subcellular RNA sequencing in situ" Sciencexpress. Feb. 27, 2014, pp. 1-6.
Lein, E. et al., "Genome-wide atlas of gene expression in the adult mouse brain," Nature, vol. 445, 2007, 168-76.
Levsky, J. et al., "Fluorescence in situ hybridization: past, present and future," Journal of Cell Science, 116, 2003, 2833-2838.
Lieberman-Aiden, E. et al., "Comprehensive mapping of long-range interactions reveals folding principles of the human genome", Science 326, 2009, 289-93.
Linder, M. E. et al. "Palmitoylation: Policing protein stability and traffic." Nature Reviews Molecular Cell Biology 8:74-84 (2007). doi:10.1038/nrm2084.
Livet, J. et al. "Transgenic strategies for combinatorial expression of fluorescent proteins in the nervous system." Nature 450, 56-62 (2007).
Lowe, D. G., "Distinctive Image Features from Scale-Invariant Keypoints," Int. J. Comput. Vis., 60, 2004, 91-110.
Lubeck, E. et al., "Single-cell in situ RNA profiling by sequential hybridization," Nature Methods, vol. 11 (4), 2014, 360-1.
Lubeck, E. et al., "Single-cell systems biology by super-resolution imaging and combinatorial labeling," Nature Methods, vol. 9, 2012, 743-8.
Mabrey, S. et al. "Investigation of phase transitions of lipids and lipid mixtures by sensitivity differential scanning calorimetry." Proc. Natl. Acad. Sci. 73(11): 3862-3866 (1976). doi:10.1073/pnas.73.11.3862.
Markwardt, M. L. et al., "An improved cerulean fluorescent protein with enhanced brightness and reduced reversible photoswitching," PLoS One, 6, 2011, e17896.
McKinney, S. A. et al., "A bright and photostable photoconvertible fluorescent protein," Nat. Methods, 6, 2009, 131-3.
Meng, H., "Localization of a Blood Pressure Quantitative Trait Locus (QTL) to a 1.7cM Interval on Rat Chromosome 9," Medical College of Ohio, dissertation, 2002, 1-158.
Menon, A. K. "Lipid modifications of proteins." in 'Biochemistry of Lipids, Lipoproteins and Membranes' 39-58 (2008). doi:10.1016/B978-044453219-0.50004-0.
Mito, M. et al., "Simultaneous multicolor detection of RNA and proteins using superresolution microscopy," Methods, doi:10.1016/j.ymeth.2015.11.007., 2015.
Mortensen, K. I. et al., "Optimized localization analysis for singlemolecule tracking and super-resolution microscopy", Nat. Methods, 7, 2010, 377-81.
Myhill, N. et al. "The subcellular distribution of calnexin is mediated by PACS-2." Mol. Biol. Cell 19:2777-2788 (2008). doi:10.1091/mbc.E07-10-0995.
Nagai, T. et al. "A variant of yellow fluorescent protein with fast and efficient maturation for cell-biological applications" Nat. Biotechnol. 20, 87-90 (2002).
Nagre, R. D. et al., "Thermosaline Resistant Acrylamide-Based Polyelectrolyte as Filtration Control Additive in Aqueous-Based Mud, Petroleum and Coal," vol. 56, No. 3. 2014, 222-230.
New England Bio Labs, Proteinase K, P8102S product datasheet. 1 page accessed Nov. 17, 2020.
Nilsson, M. et al., "RNA-templated DNA ligation for transcript ananlysis," Nucleic Acids Research, Information Retrieval Ltd., vol. 29, No. 2, Jan. 15, 2001, 578-581.
Ormo, M. et al. "Crystal structure of the Aequorea victoria green fluorescent protein." Science 273, 1392-5 (1996).
Panning, B. et al., "X chromosome Inactivation is Mediated by by Xist RNA stabilization," Cell. vol. 90, 1997, 907-16.
Chen, F., et al., "Expansion Microscopy," Science, 347(6221): pp. 543-548 (Jan. 2015).
Chen, F., et al., "Nanoscale Imaging of RNA with Expansion Microscopy," Nature Methods, 13(8): pp. 679-687 (Aug. 2016).
Tillberg, P., et al., "Protein-Retention Expansion Microscopy of Cells and Tissues Labeled Using Standard Fluorescent Proteins and Antibodies," Nature Biotechnology 34(9), pp. 987-995 (Sep. 2016).
Chang, J., et al., "Iterative Expansion Microscopy," Nature Methods, 14(6): pp. 593-603 (Jun. 2017).
Dilorenzo, F., et al., "Nanostructural Heterogeneity in Polymer Networks and Gels," Polymer Chemistry, vol. 6, pp. 5515-5528 (2015).
Orakdogen, N., et al., "Correlation Between Crosslinking Efficiency and Spatial Inhomogeneity in Poly(acrylamide) Hydrogels," Polymer Bulletin, vol. 57, pp. 631-641 (2006).
Yazici, I., et al., "Spatial Inhomogeneity in Poly(acrylic acid) Hydrogels," Polymer, vol. 46, pp. 2595-2602 (2005).
Sakai, T., et al., "Design and Fabrication of a High-Strength Hydrogel with Ideally Homogenous Network Structure from Tetrahedron-Like Macromonomers," Macromolecules, vol. 41, pp. 5379-5384 (2008).
Oshima, K., et al., "Model Polyelectrolyte Gels Synthesized by End-Linking of Tetra-Arm Polymers with Click Chemistry: Synthesis and Mechanical Properties," Macromolecules, vol. 47, pp. 7573-7580 (2014).
Alon, S. et al. Expansion sequencing: Spatially precise in situ transcriptomics in intact biological systems. Science 371, 481-+, doi:10.1126/science.aax2656 (2021).
Cahoon, C. K. et al. Superresolution expansion microscopy reveals the three-dimensional organization of the *Drosophila* synaptonemal complex. Proc Natl Acad Sci U S A 114, E6857-E6866, doi:10.1073/pnas.1705623114 (2017).
Campbell, K. R. et al. clonealign: statistical integration of independent single-cell RNA and DNA sequencing data from human cancers. Genome Biol 20, 54, doi:10.1186/s13059-019-1645-z (2019).
Chen, G. et al. Reactivity of functional groups on the protein surface: development of epoxide probes for protein labeling. J Am Chem Soc 125, 8130-8133, doi:10.1021/ja034287m (2003).
Cirillo, L. et al. UBAP2L forms distinct cores that act in nucleating stress granules upstream of G3BP1. Curr Biol 30, 698-707 e696, doi:10.1016/j.cub.2019.12.020 (2020).
Cote, A. et al. The spatial distributions of pre-mRNAs suggest post-transcriptional splicing of specific introns within endogenous genes. bioRxiv, doi:10.1101/2020.04.06.028092 (2020).
Cui, Y. et al. Fluctuation localization imaging-based fluorescence in situ hybridization (fliFISH) for accurate detection and counting of RNA copies in single cells. Nucleic Acids Res 46, e7, doi: 10.1093/nar/gkx874 (2018).

(56) References Cited

OTHER PUBLICATIONS

Cui, Y. et al. Quantitative mapping of oxidative stress response to lithium cobalt oxide nanoparticles in single cells using multiplexed in situ gene expression analysis. Nano Lett 19, 1990-1997, doi:10.1021/acs.nanolett.8b05172 (2019).
Decarreau, J. et al. Corrigendum: The tetrameric kinesin Kif25 suppresses pre-mitotic centrosome separation to establish proper spindle orientation. Nat Cell Biol 19, 740, doi:10.1038/ncb3546 (2017).
Decarreau, J. et al. The tetrameric kinesin Kif25 suppresses pre-mitotic centrosome separation to establish proper spindle orientation. Nat Cell Biol 19, 384-390, doi:10.1038/ncb3486 (2017).
Eirew, P. et al. Dynamics of genomic clones in breast cancer patient xenografts at single-cell resolution. Nature 518, 422-426, doi:10.1038/nature13952 (2015).
Falahati, H. et al., Thermodynamically driven assemblies and liquid-liquid phase separations in biology. Soft Matter 15, 1135-1154, doi:10.1039/c8sm02285b (2019).
Fecher, C. et al. Cell-type-specific profiling of brain mitochondria reveals functional and molecular diversity. Nat Neurosci 22(10), 1731-1742 doi:10.1038/s41593-019-0479-z (2019).
Gambarotto, D. et al. Imaging cellular ultrastructures using expansion microscopy (U-ExM). Nat Methods 16, 71-74, doi:10.1038/s41592-018-0238-1 (2019).
Gao, M. et al. Expansion stimulated emission depletion microscopy (ExSTED). ACS Nano 12, 4178-4185, doi:10.1021/acsnano.8b00776 (2018).
Gao, R. et al. A highly homogeneous polymer composed of tetrahedron-like monomers for high-isotropy expansion microscopy. Nat Nanotechnol 16, 698-707, doi:10.1038/s41565-021-00875-7 (2021).
Gao, R. et al. Cortical column and whole-brain imaging with molecular contrast and nanoscale resolution. Science 363 (6424), doi:10.1126/science.aau8302 (2019).
Hafner, A. S. et al., Local protein synthesis is a ubiquitous feature of neuronal pre- and postsynaptic compartments. Science 364, doi:10.1126/science.aau3644 (2019).
Halpern, A. R. et al., Hybrid structured illumination expansion microscopy reveals microbial cytoskeleton organization. ACS Nano 11, 12677-12686, doi:10.1021/acsnano.7b07200 (2017).
Hansen, M., Lee, S. J., Cassady, J. M. & Hurley, L. H. Molecular details of the structure of a psorospermin-DNA covalent/intercalation complex and associated DNA sequence selectivity. J Am Chem Soc 118, 5553-5561 (1996).
He, J. et al. Prevalent presence of periodic actin-spectrin-based membrane skeleton in a broad range of neuronal cell types and animal species. Proc Natl Acad Sci U S A 113, 6029-6034, doi:10.1073/pnas.1605707113 (2016).
Invitrogen Corporation, "Proteinase K (solution), RNA Grade", Cat. No. 25530-049, rev. date: Aug. 25, 2008, 2 pages, accessed from https://www.thermofisher.com/document-connect/document-connect.html?url=https://assets.thermofisher.com/TFS-Assets%2FLSG%2Fmanuals%2Fproteinasek_solution_man.pdf (2008).
Kao, P. et al., Transcriptional activation of *Arabidopsis zygotes* is required for initial cell divisions. Sci Rep 9, 17159, doi:10.1038/s41598-019-53704-2 (2019).
Karagiannis, E. D. et al. Expansion microscopy of lipid membranes. bioRxiv, 829903, doi:10.1101/829903 (2019).
Keenan et al., "An automated machine vision system for the histological grading of cervical intraepithelial neoplasia (CIN)," Journal of Pathology, J Pathol 2000; 192: pp. 351-362.
Koppers, M. et al. Receptor-specific interactome as a hub for rapid cue-induced selective translation in axons. Elife 8, 1-27 doi:10.7554/eLife.48718 (2019).
Kumar, A. et al. Influenza virus exploits tunneling nanotubes for cell-to-cell spread. Sci Rep 7, 1-14, 40360, doi:10.1038/srep40360 (2017).
Kunz, T. C. et al., Using Expansion Microscopy to Visualize and Characterize the Morphology of Mitochondrial Cristae. Front Cell Dev Biol 8, 617, doi: 10.3389/fcell.2020.00617 (2020).
Li, R. et al., Expansion enhanced nanoscopy. Nanoscale 10, 17552-17556, doi:10.1039/c8nr04267e (2018).
Lim, Y. et al. Mechanically resolved imaging of bacteria using expansion microscopy. PLoS Biol 17, e3000268, doi:10.1371/journal.pbio.3000268 (2019).
Martinez, G. F. et al. Quantitative expansion microscopy for the characterization of the spectrin periodic skeleton of axons using fluorescence microscopy. Sci Rep 10, 2917, doi:10.1038/s41598-020-59856-w (2020).
Mosca, T. J. et al., Presynaptic LRP4 promotes synapse number and function of excitatory CNS neurons. Elife 6, doi:10.7554/eLife.27347 (2017).
M'Saad, O. et al., Light microscopy of proteins in their ultrastructural context. Nat Commun 11, 3850, doi:10.1038/s41467-020-17523-8 (2020).
Park, Y. G. et al. Protection of tissue physicochemical properties using polyfunctional crosslinkers. Nat Biotechnol 37, 73-83, doi:10.1038/nbt.4281 (2019).
Richter, S. et al. Clerocidin alkylates DNA through its epoxide function: evidence for a fine tuned mechanism of action. Nucleic Acids Res 31, 5149-5156, doi:10.1093/nar/gkg696 (2003).
Sahl, S. J. et al., Fluorescence nanoscopy in cell biology. Nat Rev Mol Cell Biol 18(11), 685-701, doi:10.1038/nrm.2017.71 (2017).
Sarkar, D. et al. Expansion revealing: decrowding proteins to unmask invisible brain nanostructures. bioRxiv, doi:10.1101/2020.08.29.273540 (2020).
Shen, F. Y. et al. Light microscopy based approach for mapping connectivity with molecular specificity. Nat Commun 11, 4632, doi:10.1038/s41467-020-18422-8 (2020).
Shurer, C. R. et al. Physical principles of membrane shape regulation by the glycocalyx. Cell 177, 1757-1770 e1721, doi:10.1016/j.cell.2019.04.017 (2019).
Sidenstein, S. C. et al. Multicolour multilevel STED nanoscopy of actin/spectrin organization at synapses. Sci Rep 6, 26725, doi:10.1038/srep26725 (2016).
So, C. et al. A liquid-like spindle domain promotes acentrosomal spindle assembly in mammalian oocytes. Science 364, doi:10.1126/science.aat9557 (2019).
Suofu, Y. et al. Dual role of mitochondria in producing melatonin and driving GPCR signaling to block cytochrome c release. Proc Natl Acad Sci U S A 114, E7997-E8006, doi:10.1073/pnas.1705768114 (2017).
Thevathasan, J. V. et al. Nuclear pores as versatile reference standards for quantitative superresolution microscopy. Nat Methods 16, 1045-1053, doi:10.1038/s41592-019-0574-9 (2019).
Tillberg, P. W. et al. Expansion microscopy: scalable and convenient super-resolution microscopy. Annu Rev Cell Dev Biol 35, 683-701, doi:10.1146/annurev-cellbio-100818-125320 (2019).
Truckenbrodt et al., A practical guide to optimization in X10 expansion microscopy. Nat Protoc 14, 832-863, doi:10.1038/s41596-018-0117-3 (2019).
Valdes, P. A. et al. Decrowding expansion pathology: unmasking previously invisible nanostructures and cells in intact human brain pathology specimens. bioRxiv, doi: 10.1101/2021.12.05.471271 (2021).
Wang, G. et al., Multiplexed imaging of high-density libraries of RNAs with MERFISH and expansion microscopy. Sci Rep 8(4847), 1-13 doi:10.1038/s41598-018-22297-7 (2018).
Wang, Y. et al. EASI-FISH for thick tissue defines lateral hypothalamus spatio-molecular organization. Cell 184, 6361-6377 e6324, doi:10.1016/j.cell.2021.11.024 (2021).
Xu, H. et al. Molecular organization of mammalian meiotic chromosome axis revealed by expansion STORM microscopy. Proc Natl Acad Sci U S A 116, 18423-18428, doi:10.1073/pnas.1902440116 (2019).
Xu, K. et al., Actin, spectrin, and associated proteins form a periodic cytoskeletal structure in axons. Science 339, 452-456, doi:10.1126/science.1232251 (2013).
U.S. Appl. No. 18/193,886, filed Mar. 31, 2023.

* cited by examiner

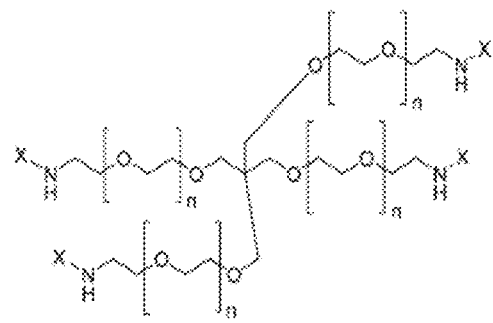
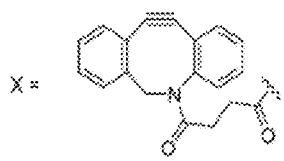
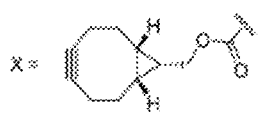
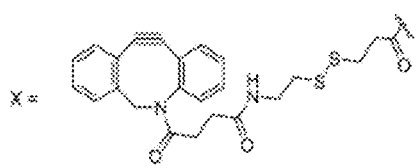
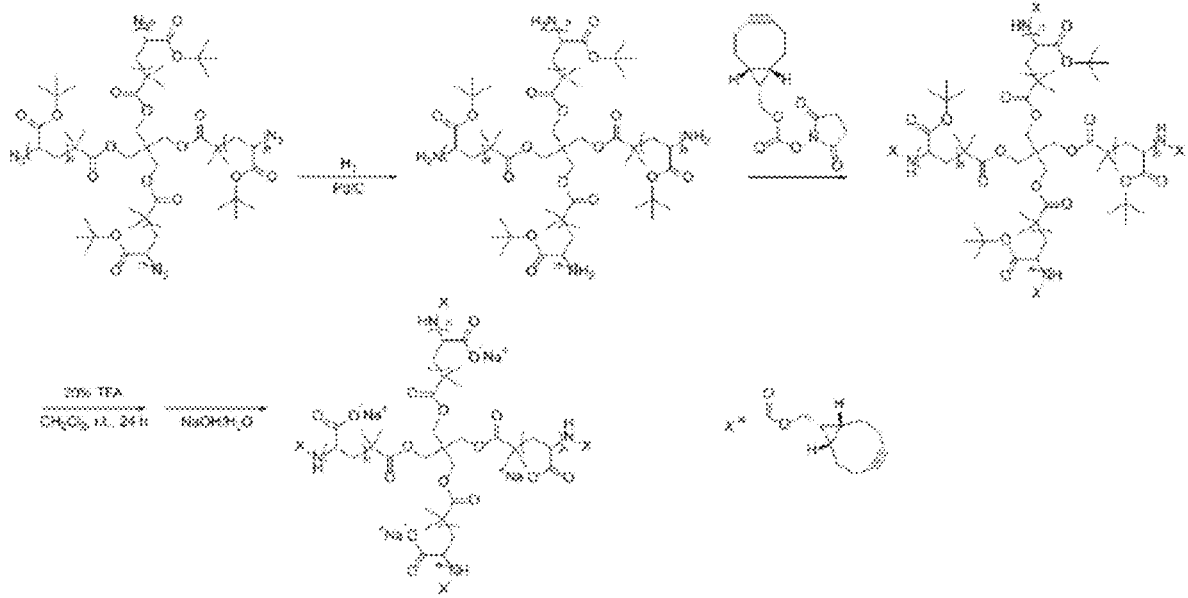
FIG. 3A and 3B

SEQUENCE LISTING

```
<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
aatacgccct aagaatccga ac                                              22

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
gttcggattc ttagggcgta                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
```
gttcggattc ttagggcgta                                               20

<210> SEQ ID NO 4
<211> LENGTH: 88
<212> TYPE: DNA
<213> ORGANISM: Artificial Sequence
<220> FEATURE:
<223> OTHER INFORMATION: Synthetic Oligonucleotide

<400> SEQUENCE: 4
tacgccctaa gaatccgaac atgcattaca gccctcaatg cattacagcc ctcaatgcat      60
tacagccctc aatgcattac agccctca                                        88

<210> SEQ ID NO 5
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 5
tacgccctaa gaatccgaac atggtgacag gcatctcaat ct                        42

<210> SEQ ID NO 6
<211> LENGTH: 88
<212> TYPE: DNA
<213> ORGANISM: Artificial Sequence
<220> FEATURE:
<223> OTHER INFORMATION: Synthetic Oligonucleotide

<400> SEQUENCE: 6
agattgagat gcctgtcacc atgcattaca gccctcaatg cattacagcc ctcaatgcat      60
tacagccctc aatgcattac agccctca                                        88

<210> SEQ ID NO 7
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 7
tgagggctgt aatgc                                                      15

SWELLABLE AND STRUCTURALLY HOMOGENOUS HYDROGELS AND METHODS OF USE THEREOF

RELATED APPLICATION

This application claims the benefit of U.S. Provisional Application No. 62/626,920, filed on Feb. 6, 2018. The entire teachings of the above application are incorporated herein by reference.

GOVERNMENT SUPPORT

This invention was made with government support under Grant No. 6936173 awarded by ARO and under Grant No. 6934416 awarded by the National Institutes of Health. The government has certain rights in the invention.

BACKGROUND OF THE INVENTION

Expansion microscopy (ExM), described for example in WO2015127183 and Chen et al., *Science*, 347, 543 (2015), is a technique that allows for three-dimensional (3D) nanoscale imaging of biological samples by physically expanding the specimens[1-4]. In ExM, hydrogels are synthesized within the biological samples. During the gelation process, biomolecules or tags are anchored to the hydrogel matrix. The hydrogel-specimen composite then goes through a 3D expansion, physically separating the biomolecules or tags.

In all of the ExM processes reported, the swellable hydrogel is synthesized by radical polymerization, a reaction known to introduce structural inhomogeneities at nanoscopic length scales[5-7]. The structural inhomogeneity is mainly caused by two factors: (a) local fluctuation of reagent concentrations during gelation and (b) topological defects such as loops and entanglements of polymer chains.

Therefore, there is a need in the art for a swellable hydrogel that is structurally homogenous down to the nanoscopic length scale.

REFERENCE TO AN ELECTRONIC SEQUENCE LISTING

The contents of the electronic sequence listing (sequence-listing.txt; Size: 1,949 bytes; Date of Creation: Sep. 6, 2023) is herein incorporated by reference in its entirety.

SUMMARY OF THE INVENTION

The invention encompasses hydrogels, monomer precursors of the hydrogels, composites comprising the hydrogel and a biological sample, methods for the preparation of the hydrogels and the composites, and methods of using the hydrogels and the composites. As described in more detail below, the hydrogels are designed to be structurally homogenous down to the nanoscopic length scale. The linking of the monomers described herein can take place using non-radical, bio-orthogonal reactions such as copper-free click-chemistry.

In some aspects, the hydrogel is the product of a non-radical polymerization reaction between a monomer of Formula A, wherein the monomer of Formula A is a monomer of Formula A1, Formula A2, Formula A3, Formula A4, Formula A5, or Formula A6.

In some aspects, the hydrogel is the product of a non-radical polymerization reaction between a monomer of Formula (A1):

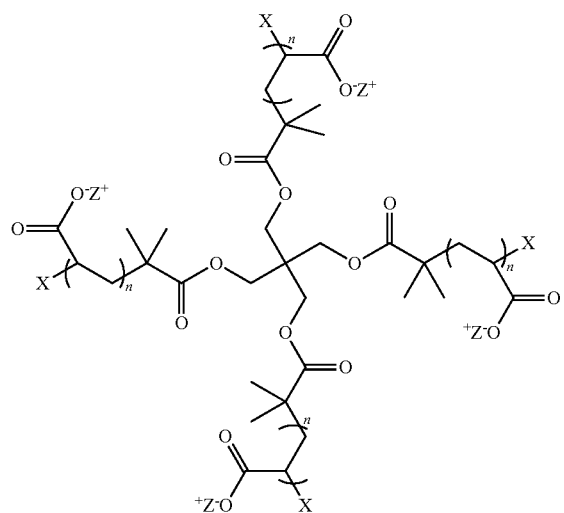

and a monomer of Formula (B1):

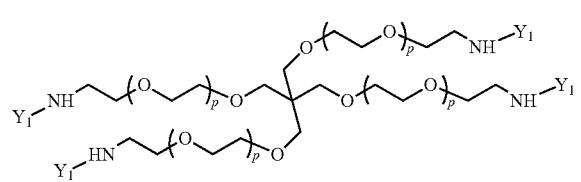

wherein: each n is an integer greater than or equal to 1; each p is an integer greater than or equal to 1; X and $Y_1$ are each crosslinkable moieties; $Z^+$ is a counter cation; and X and $Y_1$ covalently crosslink to end-link the monomers. In preferred aspects, the non-radical polymerization is bio-orthogonal. In certain aspects, X is a moiety comprising a terminal azide group and $Y_1$ is a moiety comprising a terminal alkyne and X and $Y_1$ crosslink by copper-free azide-alkyne cycloaddition.

In additional aspects, the hydrogel is the product of a non-radical polymerization reaction between a monomer of Formula (A2):

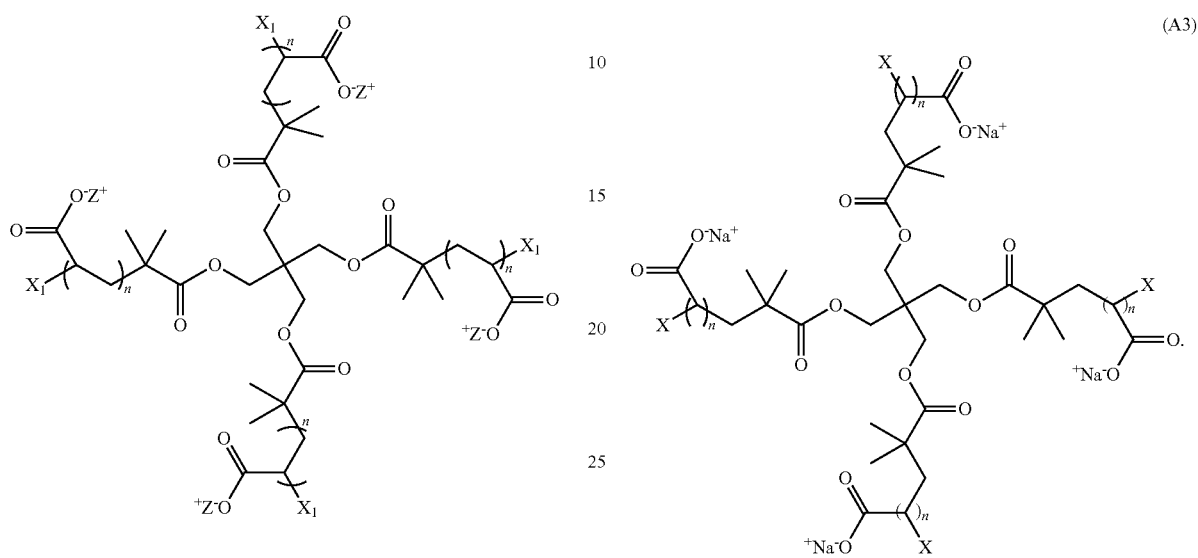

and a monomer of Formula (B2)

(B2)

wherein: each n is an integer greater than or equal to 1; each q is an integer greater than or equal to 1; $Y_2$ is a moiety comprising a terminal dibenzocyclooctyl (DBCO) or a terminal bicyclononyne; $X_1$ is a moiety comprising a terminal azide group; $Z^+$ is a counter cation; and $X_1$ and $Y_2$ crosslink by copper-free azide-alkyne cycloaddition. In preferred aspects, the non-radical polymerization is bio-orthogonal. In certain aspects, $Z^+$ is $Na^+$ or $K^+$.

In certain additional aspects, $Z^+$ is $Na^+$ or $K^+$. A non-limiting example of a monomer of Formula (A1) has the Formula (A3):

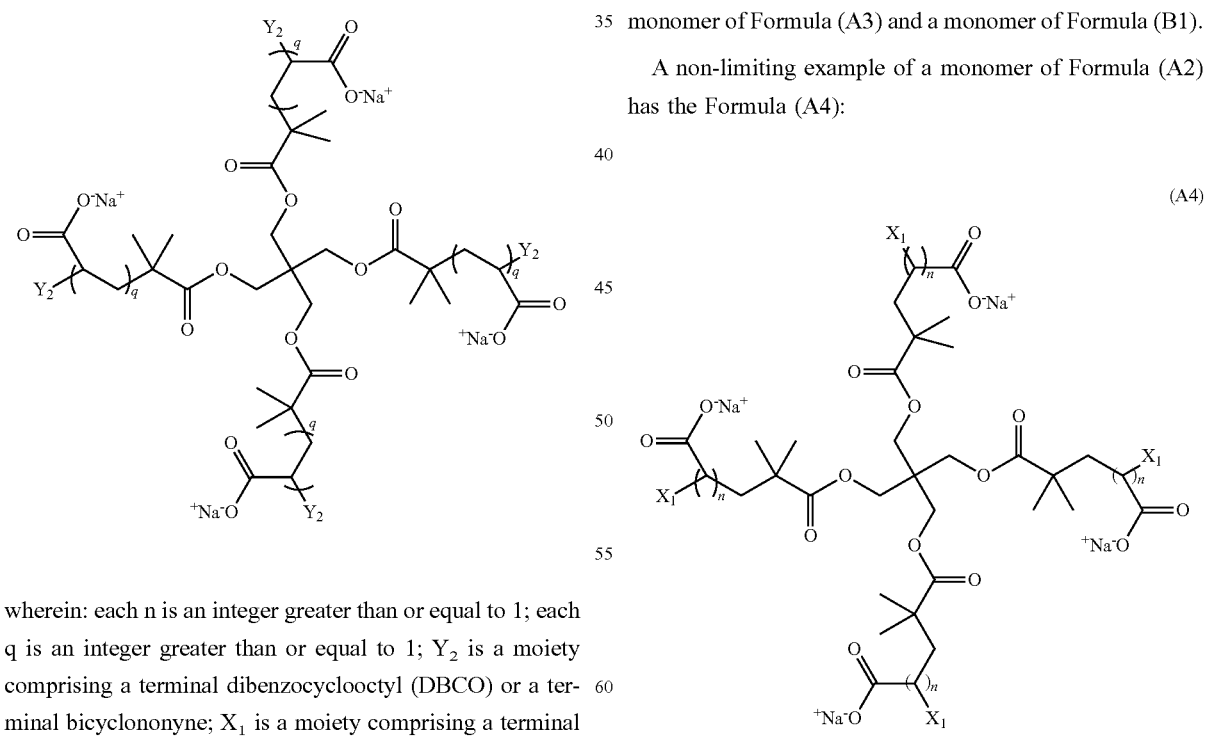

Thus, the invention also encompasses a hydrogel that is the product of a non-radical polymerization reaction between a monomer of Formula (A3) and a monomer of Formula (B1).

A non-limiting example of a monomer of Formula (A2) has the Formula (A4):

(A4)

The invention also includes a hydrogel that is the product of a non-radical polymerization reaction between a monomer of Formula (A4) and a monomer of Formula (B2).

The invention additionally encompasses a hydrogel that is the product of a non-radical polymerization reaction between a monomer of Formula (A5):

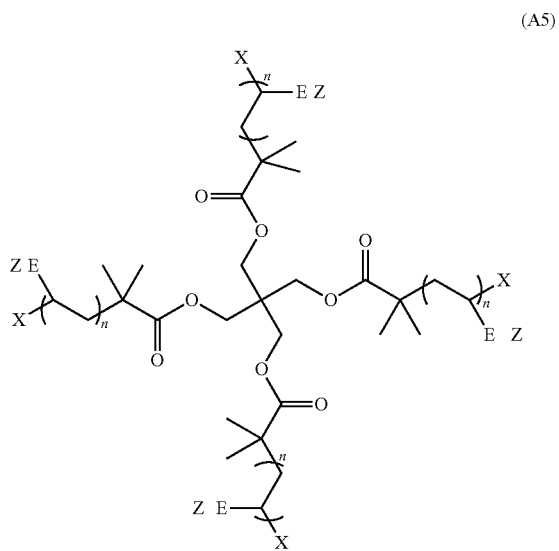

(A5)

and the monomer of Formula (B1) as described above, wherein E is a moiety comprising a charged functional group and Z is a counter ion (for example, a counter cation or counter anion depending on the charge of E); and X and n are as defined above for Formula (A1). In certain aspects, E is a charged functional group; for example, E is selected from a carboxylic acid group, an ammonium group, and a sulfate group.

The invention additionally encompasses a hydrogel is the product of a non-radical polymerization reaction between a monomer of Formula (A6):

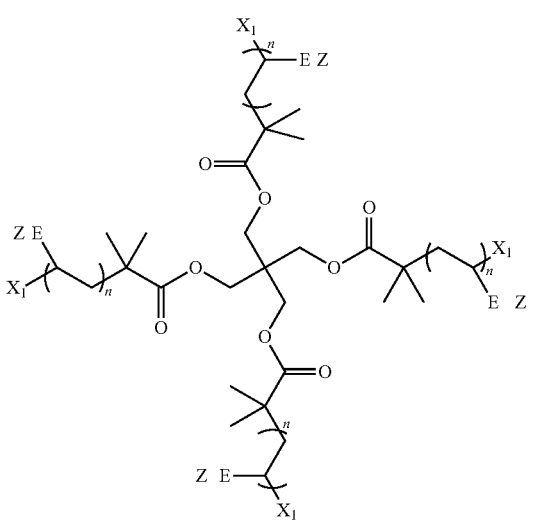

(A6)

and the monomer of Formula (B2) as described above, wherein E and Z are as defined above for Formula (A5); and X and n are as defined above for Formula (A1). In certain aspects, E is selected from a carboxylic acid group, an ammonium group, and a sulfate group.

In certain additional aspects, the invention is directed to a composite comprising a biological sample and a hydrogel that is the product of a non-radical polymerization reaction between the monomer of Formula (A1), (A2), (A3), (A4), (A5) or (A6) (collectively referred to herein as Formula (A)) and the monomer of Formula (B1). The invention also encompasses a method of preparing the composite comprising permeating the biological sample with the monomer of Formula (A1), (A2), (A3), (A4), (A5) or (A6) and the monomer of Formula (B1) under conditions suitable to form a hydrogel by non-radical polymerization.

In certain additional aspects, the invention is directed to a composite comprising a biological sample and a hydrogel that is the product of a non-radical polymerization reaction between the monomer of Formula (A2), (A4), or (A6) and the monomer of Formula (B2). The invention also encompasses a method of preparing the composite comprising permeating the biological sample with the monomer of Formula (A2), (A4), or (A6), and the monomer of Formula (B2) under conditions suitable to form a hydrogel by non-radical polymerization. In yet additional aspects, the invention is directed to a method of microscopy comprising:
  a. permeating the biological sample with a monomer of Formula (A1), (A2), (A3), (A4), (A5) or (A6) and a monomer of Formula (B1) under conditions suitable to form a hydrogel by non-radical polymerization;
  b. isotropically expanding the composite by contacting it with an aqueous solution; and
  c. viewing the expanded composite using microscopy.

In further aspects, the invention is directed to a method of microscopy comprising:
  a. permeating the biological sample with a monomer of Formula (A2), (A4), or (A6), and a monomer of Formula (B2) under conditions suitable to form a hydrogel by non-radical polymerization;
  b. isotropically expanding the composite by contacting it with an aqueous solution; and
  c. viewing the expanded composite using microscopy.

BRIEF DESCRIPTION OF THE DRAWINGS

The patent or application file contains at least one drawing executed in color. Copies of this patent or patent application publication with color drawings will be provided to the Office upon request and payment of the necessary fee.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 3A and 3B: Synthesis of one version of Monomer B based on 4-arm PEGs. (a) Using 4-arm PEG-amines as the starting material, different end groups such as (i) dibenzocyclooctyl (DBCO), (ii) bicyclononyne (BCN) or (iii) dibenzocyclooctyl-disulfide (DBCO-SS) groups can be added to the arm ends via amine/NHS ester reaction. (b) An intermediate in the Monomer A synthesis (in FIG. 2) can be further modified into a 4-arm sodium polyacrylate species with DBCO end groups and can be used as Monomer B.

DETAILED DESCRIPTION OF THE INVENTION

Figures 1A, 1B:
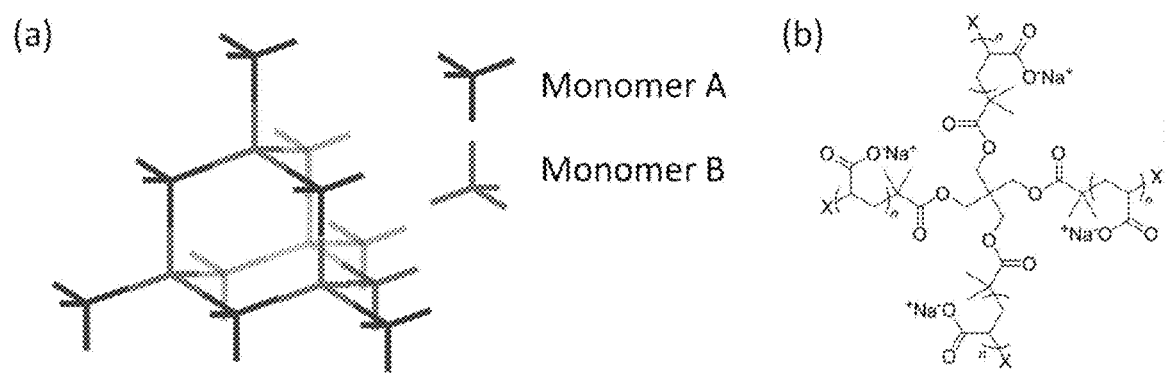
FIGS. 1A and 1B: Design of swellable, structurally homogenous hydrogels based on tetrahedral monomers. (a) Tetrahedral monomers A and B have functional end groups that specifically and complementarily bind to each other. (b) One implementation of Monomer A with repeated sodium acrylate units.

A description of preferred embodiments of the invention follows.

As used herein, the words "a" and "an" are meant to include one or more unless otherwise specified. For example, the term "a cell" encompasses both a single cell and a combination of two or more cells.

As will be apparent to those of skill in the art, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

As used herein, the terms "specimen" or "sample" are used interchangeably herein and include, but are not limited to tissues, including but not limited to, liver, spleen, kidney, lung, intestine, thymus, colon, tonsil, testis, skin, brain, heart, muscle and pancreas tissue. Other exemplary biological samples include, but are not limited to, biopsies, bone marrow samples, organ samples, skin fragments and organisms. Materials obtained from clinical or forensic settings are also within the intended meaning of the term biological sample. In one embodiment, the sample is derived from a human, animal, or plant. In one embodiment, the biological sample is a tissue sample, preferably an organ tissue sample.

In one embodiment, samples are human. The sample can be obtained, for example, from autopsy, biopsy or from surgery. It can be a solid tissue such as, for example, parenchyme, connective or fatty tissue, heart or skeletal muscle, smooth muscle, skin, brain, nerve, kidney, liver, spleen, breast, carcinoma (e.g., bowel, nasopharynx, breast, lung, stomach etc.), cartilage, lymphoma, meningioma, placenta, prostate, thymus, tonsil, umbilical cord or uterus. The tissue can be a tumor (benign or malignant), cancerous or precancerous tissue. The sample can be obtained from an animal or human subject affected by disease or other pathology or suspected of same (normal or diseased), or considered normal or healthy. The biological sample can, for example, be a cell sample. In certain aspects, the biological sample is a virus or virion. The term "biological sample" can a biological sample that comprises, or is believed to comprise, nucleic acid sequences including, but not limited to cDNA, mRNA and genomic DNA.

Tissue specimens suitable for use with the methods and systems described herein generally include any type of tissue specimens collected from living or dead subjects, such as, e.g., biopsy specimens and autopsy specimens. Tissue specimens may be collected and processed using the methods and systems described herein and subjected to microscopic analysis immediately following processing, or may be preserved and subjected to microscopic analysis at a future time, e.g., after storage for an extended period of time. In some embodiments, the methods described herein may be used to preserve tissue specimens in a stable, accessible and fully intact form for future analysis. For example, tissue specimens, such as, e.g., human brain tissue specimens, may be processed as described above and cleared to remove a plurality of cellular components, such as, e.g., lipids, and then stored for future analysis.

Tissues that have been preserved, or fixed, contain a variety of chemical modifications that can reduce the detectability of proteins in biomedical procedures. In some embodiments, the methods and systems described herein may be used to analyze a previously-preserved or stored tissue specimen. Previously preserved tissue specimens include, for example, clinical samples used in pathology including formalin-fixed paraffin-embedded (FFPE), hematoxylin and eosin (H&E)-stained, and/or fresh frozen tissue specimens. If the previously preserved sample has a coverslip, the coverslip should be removed. The sample is treated to remove the mounting medium. Such methods for removing the mounting medium are well known in the art. For example, treating the sample with xylene to remove paraffin or other hydrophobic mounting medium. Alternatively, if the sample is mounted in a water-based mounting medium, the sample is treated with water. The sample is then rehydrated and subjected to antigen-retrieval. The term "antigen retrieval" refers to any technique in which the masking of an epitope is reversed and epitope-antibody binding is restored such as, but not limited to, enzyme induced epitope retrieval, heat induced epitope retrieval (HIER), or proteolytic induced epitope retrieval (PIER). For example, the antigen retrieval treatment can be performed in a 10 mM sodium citrate buffer as well as the commercially available Target Retrieval Solution (DakoCytomation) or such.

The term "bio-orthogonal" in reference to a chemical reaction refers to a chemical reaction that does not interfere with any other chemical moieties in the natural or native surroundings.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

Monomers of Formulae (A1), (A2), (A3), (A4), (A5) and (A6) can collectively be referred to as monomers of Formula (A). Monomers of Formula (B1) and (B2) can collectively be referred to as monomers of Formula (B).

The term "hydrogel AB1" is used to refer to a hydrogel that is the product of a reaction between a monomer of Formula (A) and a monomer of Formula (B1), and the term "hydrogel AB2" is used to refer to a hydrogel that is the product of a reaction between a monomer of Formula (A) and a monomer of Formula (B2). Other hydrogel that are the product of a reaction between a monomer of Formula (A) and a monomer of Formula (B1) or (B2) can be similarly referred to.

The invention encompasses hydrogels, monomer precursors of the hydrogels, methods for the preparation of the hydrogels, and methods of using the hydrogel, for example, in expansion microscopy and/or in situ sequencing, wherein the hydrogel is the product of a non-radical polymerization reaction between a monomer of Formula (A) and a monomer of Formula (B1), or the product of a non-radical polymerization reaction between a monomer of Formula (A2), (A4), or (A6) and a monomer of Formula (B2).

In certain aspects, the invention is directed to a hydrogel that is the product of a non-radical polymerization reaction between a monomer of Formula (A1), (A2), (A3), (A4), (A5), or (A6) and a monomer of Formula (B1). In certain additional aspects, the X of Formula (A1), (A3), and/or (A5) or $X_1$ of Formula (A2), (A4), or (A6) is azide (—$N_3$) and the $Y_1$ of Formula (B1) is a cyclic alkyne.

In additional aspects, the invention is directed to a hydrogel that is the product of a non-radical polymerization reaction between a monomer of Formula (A2), (A4), or (A6), and a monomer of Formula (B2).

The invention also encompasses a monomer of Formula (A1), (A3), and (A5), in certain embodiments, X is azide. The invention additionally encompasses a monomer of Formula (A2), (A4), and (A6), wherein $X_1$ is azide. The invention additionally encompasses a monomer of Formula (B1); in certain aspects, $Y_1$ is a cyclic alkyne such as dibenzocyclooctyl (DBCO) or a bicyclononyne. In further aspects, the invention encompasses a monomer of Formula (B2); in certain aspects, X is azide.

In certain aspects, E of Formula (A5) or Formula (A6) is a negatively charged functional group. Exemplary negatively-charged groups include, without limitation, carboxylic (e.g., acetic) group, sulfo group, sulfino group, phosphate group and phosphono group. In yet additional aspects, E of Formula (A5) or Formula (A6) is a positively charged functional group. Examples of positively-charged functional groups include, without limitation, amino (amine) groups that can be protonated to form an ammonium group. In certain aspects, a charged functional group is one that exhibits a charge at, or near, neutral pH (pH of about 5 to about 9 or about 6 to about 8) in an aqueous medium.

Z is a counter ion. For example, in Formulae (A5) and (A6), if E comprises a negatively charged functional group, then Z is a counter cation, and if E comprises a positively charged functional group, then Z is a counter anion.

$Z^+$ is a counter cation such as an alkali metal atom, an alkali earth metal atom, or substituted or unsubstituted ammonium. Non-limiting examples of counter cations are potassium, sodium, mercury, lithium, magnesium, calcium, butylammonium, trimethylammonium, and tetramethyl ammonium. In certain aspects, the counter cation is sodium or potassium (Na+ or K+). In yet additional aspects, the counter cation is (Na+). In certain aspects, the monomer of Formula (A1) has the Formula (A3):

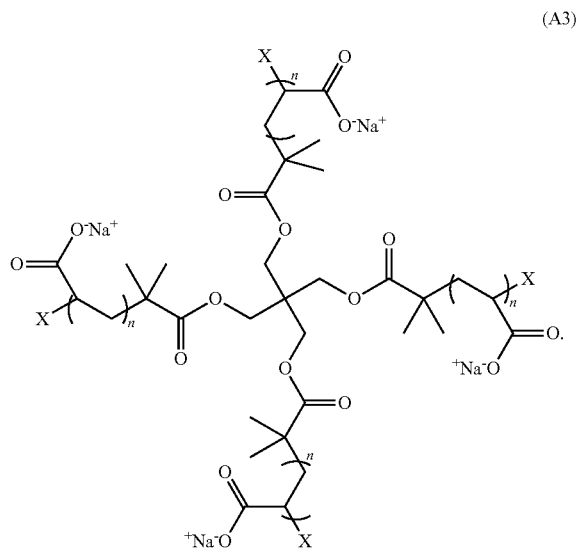

The hydrogels described herein are swellable and can be used in expansion microscopy (ExM). In ExM, chemically fixed and permeabilized tissue (or other biological sample) is infused with swellable material, undergoes polymerization, and the tissue-polymer composite is treated to homogenize its mechanical characteristics. Next, dialysis in water or aqueous solution results in isotropic expansion, thereby achieving super-resolution with diffraction-limited microscopes, and enabling rapid image acquisition and large field of view (Chen et al., Science, 347, 543 (2015)). Expansion allows individual nucleic acids, normally densely packed, to be resolved spatially in a high-throughput manner. Furthermore, the expanded environment is 99% water, facilitating enzyme access and creating "quasi-in vitro" environment while retaining spatial information. In some examples, fixation of the biological sample can be effected by embedding the sample in a swellable material that has been perfused throughout the sample as described by Chen et al. (Chen et al., Science, 347, 543 (2015) and U.S. Patent Publication Nos. US 20160116384-A1; US 20160305856-A1; US 20160304952-A1; and U.S. Patent Publication Nos. US 20170067096 A1 and US 20170089811 A1, each corresponding to U.S. patent application Ser. Nos. 15/229,539 and 15/229,545, respectively, the contents of each of which are incorporated herein by reference in their entirety. Briefly, a sample, such as tissue, can be permeabilized. A permeabilized sample, or tissue, can be infused with monomers or precursors of a swellable material and then causing the monomers or precursors to undergo polymerization within the sample to form the swellable material. During or after polymerization, the swellable material can be anchored to the sample. The sample-hydrogel complex (or composite) is optionally treated to homogenize the mechanical characteristics of the sample. The sample-swellable material complex can then be treated by dialysis in a solvent or liquid, such as in water, resulting in isotropic physical expansion of the sample. In this manner, the fixed biological sample is physically "enlarged", or "expanded", as compared to the biological sample before swelling.

The swellable hydrogels currently being used in expansion microscopy (ExM) are synthesized by radical polymerization which is known to introduce structural inhomogeneities at nanoscopic length scale. The structural inhomogeneity is mainly caused by two factors: (a) local fluctuation of reagent concentrations during the gelation and (b) topological defects such as loops and entanglements of polymer chains. To eliminate these intrinsic structural inhomogeneities, the hydrogels described herein have been designed which are structurally homogenous down to the nanoscopic length scale. For example, two types of pre-synthesized tetrahedral monomers are linked in a diamond lattice-like structure. The linking of the monomers takes place using non-radical, bio-orthogonal reactions including, but not limited to, copper-free click-chemistry. In this new hydrogel design, the homogeneity in monomer shape and size mitigates the effect of reagent concentration variations described in (a) above, resulting in a more uniform distribution of monomers and cross-links throughout the gel. Furthermore, the specific and complementary linking chemistry between the monomers reduces topological defects caused by (b) and thus facilitates formation of a homogeneous and isotropic polymer network.

It has been shown that a non-swellable hydrogel with similar diamond lattice-like structure to the hydrogel described herein is structurally homogeneous and has nearly zero defects'. Specifically, Sakai and colleagues demonstrated that end-linked tetrahedral monomers based on polyethylene glycol (PEG) can form highly homogeneous hydrogel networks free of defects'. These hydrogels, however, exhibit minimal expansion (~1.3× volume) and thus cannot be directly used in ExM. Oshima and colleagues investigated expandable hydrogels based on charged tetrahedral polyacrylate monomers, finding that this network is structurally superior to polyacrylate gels formed via radical polymerization in terms of sol fractions, dangling chains and trapped entaglements[9]. However, this strategy for gel formation required (1) copper catalysis and (2) treatment with trifluoroacetic acid, which are unlikely to be compatible with biological specimens.

In contrast to the gels of Sakai and Oshima, the hydrogels of the present invention are capable of isotropically expanding and are prepared using non-radical, bio-orthogonal reactions to end-link monomers. As described above, the lengths between cross-linkers (i.e., the "mesh size") need to be uniform in order to eliminate structural inhomogeneities in hydrogels. In addition, topological defects, such as entanglements, loops and dangling chains, need to be significantly reduced. The use of pre-synthesized monomers of defined arm lengths which are linked in a periodic fashion results in the formation of a hydrogel with structural homogeneity. For instance, two kinds of homogeneous tetrahedral monomers (Monomer A and Monomer B shown in FIG. 1A) can be linked to form a diamond lattice-like polymer network (FIG. 1A). In this design, monomers of Formula (A) and monomers of Formula (B1) or (B2) have specific and complementary linkers that bind two arms in between the two monomers. The linking needs to be covalent so that when the hydrogel physically expands in water, the monomers will stay linked and the diamond lattice-like structure will be maintained.

In swellable hydrogels (in particular, those swelling in water), the polymer chains commonly have charged functional groups so that the charges can repel each other and pull the polymer chains apart. For instance, in the polyacrylamide/sodium polyacrylate hydrogels that have been described for use in ExM, the polymer chains have carboxylate groups that are negatively charged in water ("polyelectrolyte"). The repulsion between the negative charges help to keep the hydrogel expanded in water. In an example of the present design of tetrahedral monomers, the monomers (specifically, the monomers of Formula (A) and/or monomers of Formula (B2)) include repeats of sodium acrylate groups in each arm to make the monomer charged in water. For example, a monomer of Formula (A) and/or a monomer of Formula (B2) can include repeats of sodium acrylate units in each arm of the monomer (FIG. 1B). The hydrogels can also be prepared using a monomer of Formula (A) that includes repeats of ionized or charged functional groups other than carboxylate. Such monomers are encompassed by Formulae (A5) and (A6). For example, the repeating functional group can be ammonium or sulfate.

The mesh size of the hydrogel can be systematically controlled by synthetically changing the arm lengths of the monomers ("n" in the Formula (A), "p" in Formulae (B1) and "q" in Formula (B2)). In certain aspects, n of the Formulae (A) is 1 to 100. In yet additional aspects, n is 4, or 10, or 20, or 40. In yet additional aspects, the monomer of Formula (A) has a molecular weight from about 0.5 kDa to about 50 kDa, or about 1 kDa to about 40 kDa, or about 1 kDa to about 25 kDa. By way of example, the monomer of Formula (A3), wherein n is 4, 10, 20 or 40, has an approximate molecular weight of 2 kDa, 5 kDa, 10 kDa, and 20 kDa, respectively.

In certain additional aspects, p of Formula (B1) is 1 to 100. In yet additional aspects, p of Formula (B1) is 36, or 72, or 144. In yet additional aspects, the monomer of Formula (B1) has a molecular weight from about 10 kDa to about 300 kDa, or about 15 kDa to about 200 kDa, or about 15 kDa to about 150 kDa. By way of example, the monomer of Formula (B1), wherein p is 36, 72 and 144, the monomer has an approximate molecular weight of about 5 kDa, 10 kDa, and 20 kDa, respectively.

In certain additional aspects, q of Formula (B2) is 1 to 100. In yet additional aspects, q is 36, 72, or 144.

As described above, the two monomers (a monomer of Formula (A) and a monomer of Formulae (B1) or (B2)) are end-linked to form a lattice-like polymer network. Each of X and $Y_1$, $X_1$ and $Y_1$, X and $Y_2$, and $X_1$ and $Y_2$ are complementary, reactive end-groups that are capable of forming a covalent bond. For example, in certain aspects, X is a moiety comprising a terminal azide group and $Y_1$ is a moiety comprising a terminal alkyne, for example, a cyclic alkyne, and X and $Y_1$ crosslink by copper-free azide-alkyne cycloaddition. In certain additional aspects, X or $X_1$ is azide ($-N_3$). $Y_1$ can, for example, be a cyclic alkyne moiety such as a moiety comprising a terminal dibenzocyclooctyl (DBCO) or a terminal bicyclononyne. Exemplary cyclic alkyne moieties include, but are not limited to, DBCO, DBCO-SS (dibenzocyclooctyl-disulfide), DBCO-amine, DBCO-N-hydroxysuccinimidyl ester, (1R,8S,9s)-bicyclo[6.1.0]non-4-yn-9-ylmethyl N-succinimidyl carbonate and DBCO-maleimide. In yet additional aspects, $Y_1$ is selected from the group consisting of:

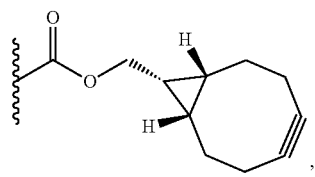

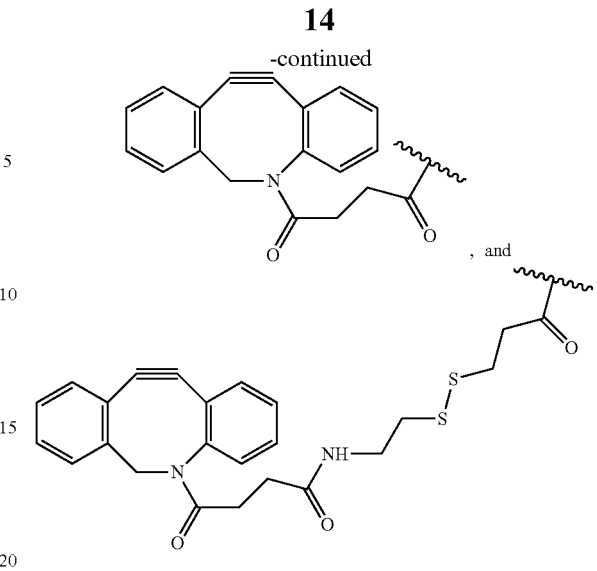

The linking chemistry between the monomers is not limited to the catalyst-free click-chemistry described above. Other linking chemistries include other bio-orthogonal reactions including, but not limited to, amine-NETS reaction, maleimide-thiol reaction, and trans-cyclooctene/s-tetrazine reaction. Therefore, in some embodiments, wherein X and $Y_1$ crosslink by amine-NETS ester reaction. For example, X can be a moiety comprising a terminal amine and $Y_1$ can be a terminal N-hydroxysuccinimide ester group. Alternatively, X can be a moiety comprising a terminal N-hydroxysuccinimide ester group and $Y_1$ can be a terminal amine. In another example, X and $Y_1$ crosslink by maleimide-thiol reaction. For example, X can be a moiety comprising a terminal sulfhydryl group and $Y_1$ can be a moiety comprising a terminal maleimide group. Alternatively, X can be a moiety comprising a terminal maleimide group and $Y_1$ can be a moiety comprising a terminal sulfhydryl group. In yet an additional example, X and $Y_1$ crosslink by trans-cyclooctene (TCO)-tetrazine reaction.

Figure 2:
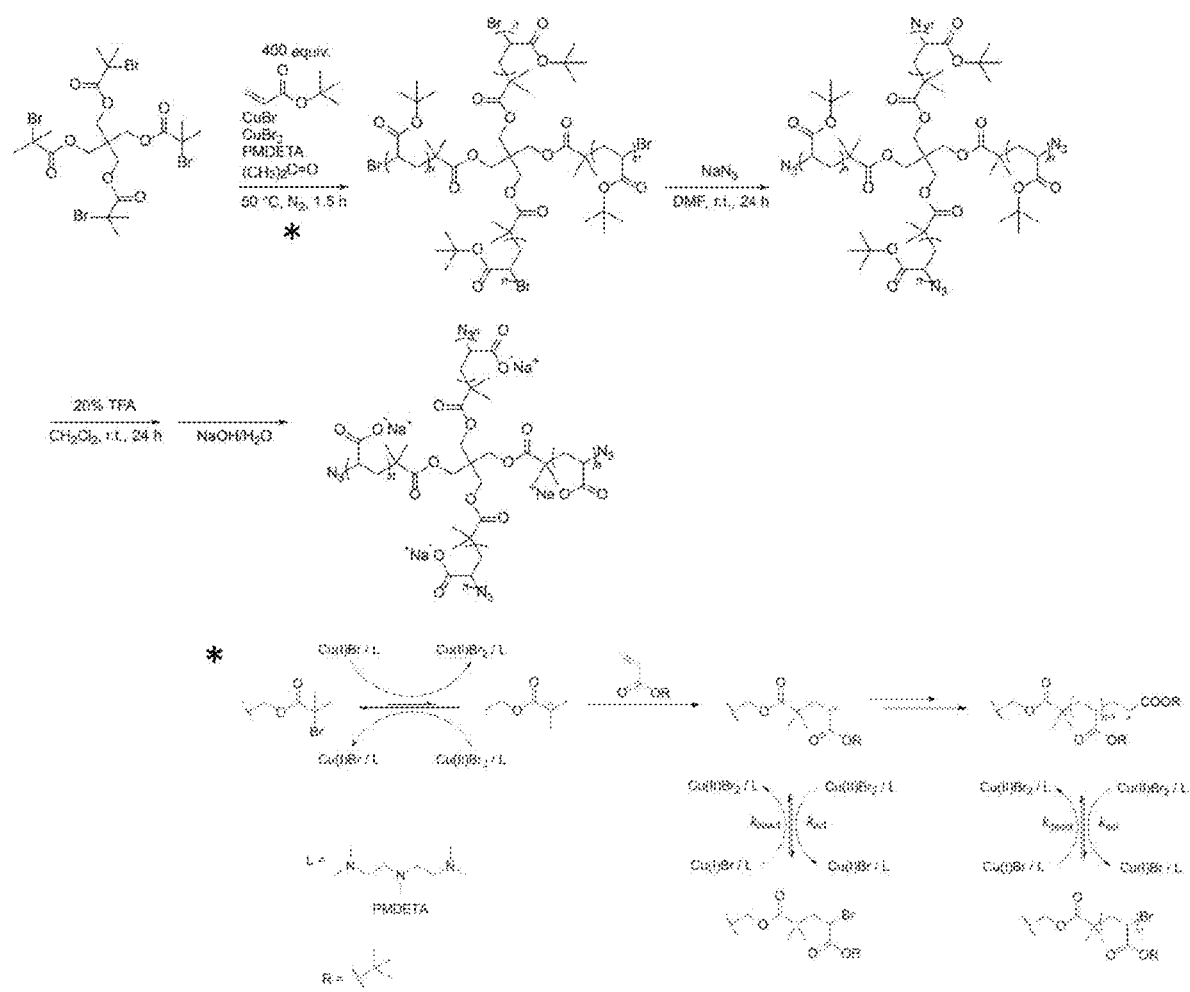
FIG. 2: Synthesis of one version of Monomer A (shown in FIG. 1B) based on the 4-arm sodium polyacrylate structure. The synthesis starts with arm elongation via atom transfer radical polymerization (synthetic details shown as "*") of tert-butyl acrylate. The bromide end groups are further modified to azide end groups for copper click-chemistry used to link the monomers. The tert-butyl polyacrylate arms are then deprotected to yield Monomer A.

In one example, the Monomer A (a monomer of Formula (A)) as shown in FIG. 1B can be synthesized via atom transfer radical polymerization (ATRP) and subsequent synthetic modifications (FIG. 2)[9]. First, tert-butyl acrylates are added to a 4-arm tetrahedral core to the desired arm length via ATRP ("*" in FIG. 2). In contrast to the conventional radical polymerization, ATRP offers site-specific and controlled addition of acrylate units to the growing polymer chains. The end groups of the monomer arms are then modified from bromide to azide for copper-free click chemistry. Finally, tert-butyl groups on the monomer arms are deprotected by a strong acid to yield Monomer A with 4-arm sodium polyacrylate structure.

Monomer B (a monomer of Formula (B1)) can be synthesized by end-functionalization of commercially available 4-arm PEG-amines (FIG. 3A). The end groups of the 4-arm PEG monomers can be modified to, for example, (i) dibenzocyclooctyl (DBCO), (ii) bicyclononyne (BCN) or (iii) dibenzocyclooctyl-disulfide (DBCO-SS) groups, all of which are reactive to the azide groups of Monomer A via copper-free click chemistry. BCN reacts more slowly with azide than DBCO or DBCO-SS and thus is more suitable for biological samples that require longer diffusion time through the specimens before the gelation begins, such as intact tissue samples. DBCO-SS can be cleaved by, for example, dithiothreitol (DTT). Therefore, the synthesized gel can be broken down at monomer level after expansion, making it compatible with processes that require breaking of the first hydrogel, such as the iterative ExM (iExM) process[4] described, for example in U.S. Pat. App. Pub. No. 20160305856A1, the contents of which are expressly incorporated by reference herein. Other monomers of Formula (B1) can be prepared using a similar process.

A modified version of 4-arm sodium polyacrylate (a monomer of Formula (B2)) can also be used as Monomer B when its end groups are modified to functional groups that are reactive to azide, such as DBCO (FIG. 3B). Other monomers of Formula (B2) can be prepared using a similar process. Using a monomer of Formula (B2), the expansion factor of the hydrogel can potentially be even larger than a hydrogel using a monomer of Formula (B1) due to the increased negative charges on both monomers in water.

Figure 4:
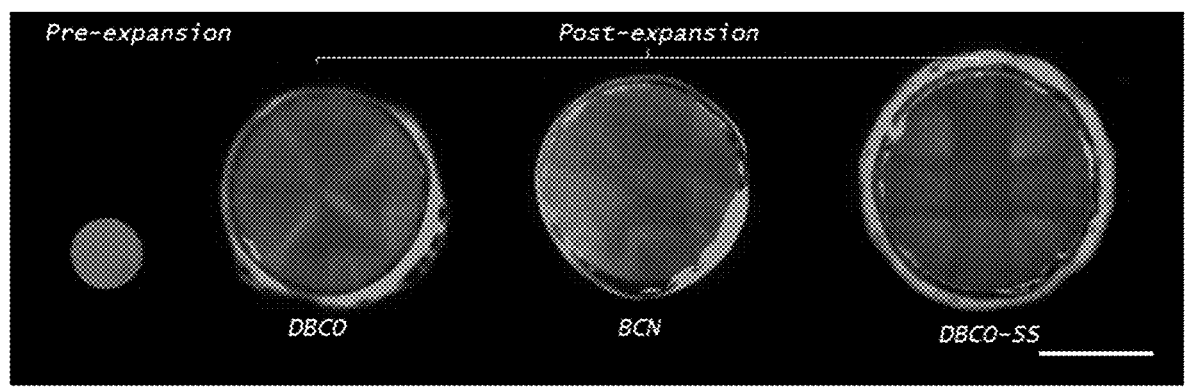
FIG. 4: Synthesis and expansion of hydrogel (termed as "tetragel") formed by reacting Monomer A and Monomer B. Fluorescence images of tetragels after expansion using three different Monomers B with the end groups specified in FIG. 3a-i (DBCO), 3a-ii (BCN) and 3a-iii (DBCO-SS) are shown. Fluorescent image of the tetragel before expansion (the pre-expansion size is the same for all three versions of Monomer B) is shown on the left for comparison. About 1 mol % fluorescein amine was anchored to the hydrogel matrix with NHS-azide to fluorescently visualize the gels. Scale bar, 5 mm.

The synthesis of the hydrogel takes advantage of the specific and complementary reaction between the monomers. For example, using Monomer A in FIG. 2B and Monomer B in FIG. 3A, a hydrogel (also termed a "tetragel") can be formed by simply mixing the two monomers in water. The click-reaction between the two monomers proceeds without copper catalyst. As an example, 10 uL of 4-arm sodium polyacrylate with azide end groups (200 mg/mL water, molecular weight ~10 kDa, shown in FIG. 2B), 10 uL of 4-arm PEG with BCN end groups (200 mg/mL DMSO, molecular weight ~10 kDa, shown in FIG. 3a-i), and 40 uL of water are mixed and then gelled at 37° C. for 2 hours. The synthesized hydrogel expands by a factor of about three-times in water (FIG. 4). As described above, the linking chemistry between the monomers is not limited to the catalyst-free click-chemistry described above. Other linking chemistries include, but are not limited to, amine-NETS reaction, maleimide-thiol reaction, and trans-cyclooctene/s-tetrazine reaction.

The invention encompasses a composite comprising a biological sample and a hydrogel described herein (e.g., the hydrogel AB1 or the hydrogel AB2). In certain aspects, a biological sample can be embedded in a hydrogel as described herein. "Embedding" a sample in a swellable material or a swellable hydrogel comprises permeating (such as, perfusing, infusing, soaking, adding or other intermixing) the sample with the swellable material, preferably by adding precursors thereof. The sample may be permeated (such as, perfusing, infusing, soaking, adding or other intermixing) with the precursors of the swellable material, wherein the sample is saturated with precursors of the swellable material, which flow between and around biomolecules throughout the specimen. Polymerizing the monomers or precursors is initiated to form the swellable material or polymer in situ, wherein the polymer network is formed within and throughout the specimen. In this manner the biological sample is embedded in the swellable material.

The invention encompasses a method of preparing a composite comprising a biological sample and a hydrogel described herein comprising permeating the sample, for example, a biological sample, with a monomer of Formula (A), for example a monomer of formula (A1), (A2), (A3), (A4), (A5), or (A6), and a monomer of Formula (B1), or a monomer of Formula (A2), (A4) or (A6), and a monomer of Formula (B2) under conditions suitable to form a hydrogel by non-radical polymerization; and isotropically expanding the composite by contacting it with an aqueous solution. The monomer of Formula (A) and Formula (B1) or Formula (B2) can be added to the sample in separate solutions or as part of a single solution (for example, similar to the gelling solution described in the Examples). Permeating the sample entails, for example, perfusing, infusing, soaking, adding, or otherwise intermixing) with the monomers or with the precursors of the hydrogel. In order to prepare the composite, the precursors (for example, a monomer of Formula (A) and monomer of Formula (B1)) can be reacted to form a hydrogel in situ. The monomers, can for example, be in solution, such as an aqueous solution. The solution can be a high concentration solution, such as about 50% or more saturation (defined herein as the percentage of solids present in the aqueous solvent in the same ratio as would result in precipitation under the conditions of permeation). In certain aspects, the solution is at high concentration, such as about 75% or more saturation, or 90% or more saturation.

In certain embodiments, the biological sample is permeated with the monomers, solutions comprising the monomers or hydrogel precursors, or a solution comprising the monomers (a monomer of Formula (A) and a monomer of Formula (B1), or a monomer of Formula (A) and a monomer of Formula (B2)) which are reacted to form a swellable polymer.

The hydrogels described herein are swellable. As used herein, the term "swellable" in reference to a hydrogel generally refers to a hydrogel that expands when contacted with a liquid, such as water or other solvent. In one embodiment, the swellable hydrogel of the present invention uniformly expands in three (3) dimensions. Additionally or alternatively, the hydrogel can be transparent such that, upon expansion, light can pass through the sample. In one embodiment, the swellable hydrogel is formed in situ from precursors thereof.

In certain embodiments, the biological sample, or a labeled sample (as described in more detail below), can, optionally, be treated with a detergent prior to being contacted with the precursors or monomers. The use of a detergent can improve the wettability of the sample or disrupt the sample to allow the precursor or monomers to permeate throughout sample.

An expandable biological sample can be prepared by contacting the sample with a bi-functional linker comprising a binding moiety and an anchor, wherein the binding moiety binds to biomolecules in the sample; permeating the sample with a composition comprising precursors of a swellable hydrogel; and initiating polymerization to form a swellable hydrogel, wherein the biomolecules are anchored to the swellable hydrogel to form a sample-swellable hydrogel complex. The precursors of a swellable hydrogel comprise the monomers as described herein (i.e., a monomer of Formula (A) and a monomer of Formula (B1), or a monomer of Formula (A) and a monomer of Formula (B2)), which are reacted to form a swellable hydrogel.

In one embodiment, the method for preparing an expandable biological specimen comprises the steps of treating the specimen with a bifunctional crosslinker; permeating the specimen with precursors of a swellable polymer; polymerizing the precursors to form a swellable polymer within the specimen; and incubating the specimen with a non-specific protease in a buffer comprising a metal ion chelator, a nonionic surfactant, and a monovalent salt. In one embodiment, the method can further comprise the step contacting the sample with macromolecules that will bind to biomolecules within the sample. The precursors of a swellable hydrogel comprise the monomers as described herein (i.e., a monomer of Formula (A) and a monomer of Formula (B1), or a monomer of Formula (A) and a monomer of Formula (B2)), which are reacted to form a swellable hydrogel.

The expandable specimen can be expanded by contacting the swellable polymer with a solvent or liquid to cause the swellable polymer to swell.

In one embodiment, prior to the treating step, the sample is subjected to any suitable antigen retrieval process known to one of skill in the art and as further described below.

In one embodiment, the method comprises incubating the specimen with about 1 to about 100 U/ml of a non-specific protease in a buffer having a pH between about 4 and about 12, the buffer comprising about 5 mM to about 100 mM of a metal ion chelator; about 0.1% to about 1.0% of a nonionic surfactant; and about 0.05 M to about 1.0 M monovalent salt. In one embodiment, the sample is incubated for about 0.5 to about 3 hours at about 50° C. to about 70° C.

By "biomolecules" it is generally meant, but not limited to, proteins, lipids, steroids, nucleic acids, and sub-cellular structures within a tissue or cell.

By "macromolecules" is meant proteins, nucleic acids, or small molecules that target biomolecules within the specimen. These macromolecules are used to detect biomolecules within the specimen and/or anchor the biomolecules to the swellable polymer. For example, macromolecules may be provided that promote the visualization of particular cellular biomolecules, e.g., proteins, lipids, steroids, nucleic acids, etc. and sub-cellular structures. In some embodiments, the macromolecules are diagnostic. In some embodiments, the macromolecules are prognostic. In some embodiments, the macromolecules are predictive of responsiveness to a therapy. In some embodiments, the macromolecules are candidate agents in a screen, e.g., a screen for agents that will aid in the diagnosis and/or prognosis of disease, in the treatment of a disease, and the like.

As used herein a bi-functional linker comprises reactive groups to functional groups (e.g., primary amines or sulfhydryls) on biomolecules within the sample and a swellable hydrogel reactive group.

The bi-functional linker may be used to chemically modify the functional group of biomolecules with a swellable hydrogel functional group, which enables biomolecules within the sample to be directly anchored to, or incorporated into, the swellable hydrogel. In one embodiment, the bifunctional linker is a hetero-bifunctional linker. Hetero-bifunctional linkers possess different reactive groups at either end of a spacer arm, i.e., atoms, spacers or linkers separating the reactive groups. These reagents not only allow for single-step conjugation of molecules that have the respective target functional group, but they also allow for sequential (two-steps) conjugations that minimize undesirable polymerization or self-conjugation. The bi-functional linker may be a small molecule linker or a nucleic acid adaptor. In some embodiments the bifunctional linker is cleavable and can be referred to herein as a cleavable crosslinker.

The anchor may be a physical, biological, or chemical moiety that attaches or crosslinks the sample to the hydrogel. This may be accomplished by crosslinking the anchor with the swellable hydrogel, such as during or after the polymerization, i.e., in situ formation of the swellable hydrogel. The anchor may comprise a polymerizable moiety. The anchor may include, but is not limited to, vinyl or vinyl monomers such as styrene and its derivatives (e.g., divinyl benzene), acrylamide and its derivatives, butadiene, acrylonitrile, vinyl acetate, or acrylates and acrylic acid derivatives. The polymerizable moiety may be, for example, an acrylamide modified moiety that may be covalently fixed within a swellable hydrogel.

As used herein, a "nucleic acid adaptor" is a nucleic acid sequence having a binding moiety capable of attaching to a nucleic acid and an anchor moiety capable of attaching to the swellable hydrogel. Attaching the nucleic acid adaptor to a nucleic acid may be accomplished by hybridization or by ligation in situ. For example, DNA adaptors may be ligated to the 3' ends of the RNAs in the sample with RNA ligases, such as T4 RNA ligase, or may be attached via a chemical linker such as a reactive amine group capable of reacting with nucleic acid. Acrylamide modified oligonucleotide primers may be covalently fixed within a swellable hydrogel such as a polyacrylate gel. As used herein, the term "acrylamide modified" in reference to an oligonucleotide means that the oligonucleotide has an acrylamide moiety attached to the 5' end of the molecule.

As used herein, a "small molecule linker" is a small molecule having a binding moiety capable of attaching to a biomolecule within the sample and an anchor moiety capable of attaching to the swellable hydrogel. Attaching the small molecule linker to the biomolecules may be accomplished by hybridization or by a chemical reactive group capable of covalently binding. For example, LABEL-IT® Amine (MirusBio) is a small molecule with alkylating group that primarily reacts to the $N_7$ of guanine, thereby allowing covalent binding of RNA and DNA. The small molecule linker may be, for example, acrylamide modified and therefore may be covalently fixed within a swellable hydrogel. As used herein, the term "acrylamide modified" in reference to a small molecule linker means that the small molecule linker has an acrylamide moiety.

In one embodiment, the bifunctional crosslinker comprises a protein-reactive chemical moiety and a swellable hydrogel-reactive chemical moiety. The protein-reactive chemical group includes, but is not limited to, N-hydroxysuccinimide (NHS) ester, thiol, amine, maleimide, imidoester, pyridyldithiol, hydrazide, phthalimide, diazirine, aryl azide, isocyanate, or carboxylic acid, which, for example, can be reacted with amino or carboxylic acid groups on proteins or peptides. In one embodiment, the protein-reactive groups include, but are not limited to, N-succinimidyl ester, pentafluorophenyl ester, carboxylic acid, or thiol. The gel-reactive groups include, but are not limited to, vinyl or vinyl monomers such as styrene and its derivatives (e.g., divinyl benzene), acrylamide and its derivatives, butadiene, acrylonitrile, vinyl acetate, or acrylates and acrylic acid derivatives.

In one embodiment, the chemical to anchor proteins directly to any swellable polymer is a succinimidyl ester of 6-((acryloyl)amino)hexanoic acid (acryloyl-X, SE; abbreviated "AcX"; Life Technologies). Treatment with AcX modifies amines on proteins with an acrylamide functional group. The acrylamide functional groups allows for proteins to be anchored to the swellable polymer as it is synthesized in situ.

As used herein, the term "attach" or "attached" refers to both covalent interactions and noncovalent interactions. In certain embodiments of the invention, covalent attachment may be used, but generally all that is required is that the bi-functional linker remain attached to the biomolecules. The term "attach" may be used interchangeably herein with the terms, "anchor(ed)", affix(ed), link(ed) and immobilize(d).

In certain embodiments, the biological sample can be labelled or tagged with a detectable label. Typically, the label will bind chemically (e.g., covalently, hydrogen bonding or ionic bonding) to the sample, or a component thereof. The detectable label can be selective for a specific target (e.g., a biomarker or class of molecule), as can be accomplished with an antibody or other target specific binder. The detectable label preferably comprises a visible component, as is typical of a dye or fluorescent molecule; however, any signaling means used by the label is also contemplated. A fluorescently labeled biological sample, for example, is a biological sample labeled through techniques such as, but not limited to, immunofluorescence, immunohistochemical or immunocytochemical staining to assist in microscopic analysis. Thus, the detectable label is preferably chemically attached to the biological sample, or a targeted component thereof. In one embodiment, the detectable label is an antibody and/or fluorescent dye wherein the antibody and/or fluorescent dye, further comprises a physical, biological, or chemical anchor or moiety that attaches or crosslinks the sample to the composition, hydrogel or other swellable material. In one embodiment, the detectable label is attached to the nucleic acid adaptor. The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of the sample.

The biological sample can be anchored to a swellable hydrogel before expansion. The anchoring can be accomplished by anchoring the bifunctional crosslinker with the swellable hydrogel, such as during or after the polymerization or in situ formation of the swellable hydrogel.

In some embodiments, the bifunctional crosslinker is attached to the X or $X_1$ moiety of the monomer of Formula (A), $Y_1$ of the monomer of Formula (B1), or $Y_2$ of the monomer of Formula (B2). The bifunctional crosslinker may comprise a small molecule linker capable of attaching to the biological sample and to the hydrogel. Examples of small molecule linkers include NHS-azide and NHS-DBCO which can react with the arms of the monomers of the hydrogel. For example, a protein and/or an antibody can be anchored to the hydrogel with NHS-azide or DBCO-NHS. In the case of NHS-azide, the NHS moiety binds to the label and the azide reacts with an alkyne group in the hydrogel (e.g., $Y_1$ or $Y_2$ of Formulae (B1) and (B2)) (for example, DBCO) by click chemistry. In the case of NHS-DBCO, the NHS moiety binds to the label and the DBCO reacts with an azide (e.g., X of Formula (A)) in the hydrogel by click chemistry.

Figure 5A:
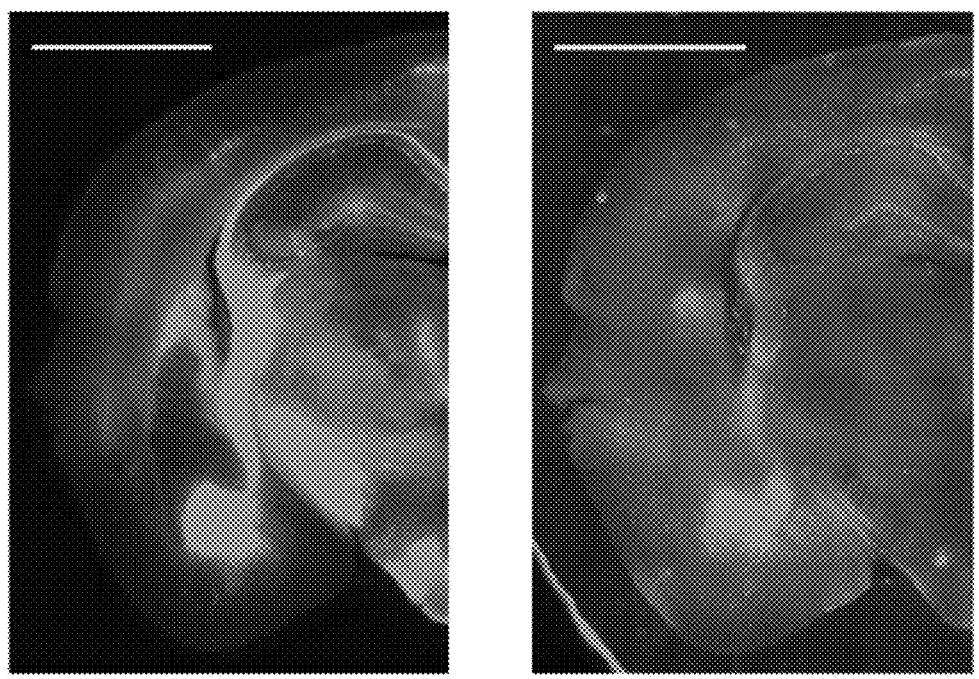
FIG. 5A: In situ synthesis and expansion of brain tissue with tetragel. Fluorescence images of the same Thy1-YFP mouse brain slice before (left) and after (right) expansion with tetragel. The post-expansion sample was immunostained by anti-GFP primary antibodies and dye-conjugated secondary antibodies. Scale bar: 2 mm (left) and 6 mm (right).
Figure 5B:
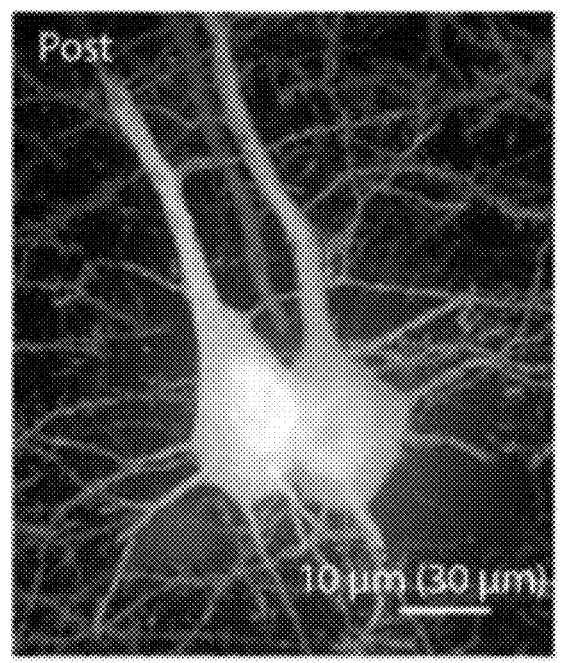
FIG. 5B: Post-expansion Thy1-YFP mouse brain slices. Scale bar, 10 µm (right, 30 µm)
Figures 6A, 6B, 6C, 6D, 6E, 6F, 6G:
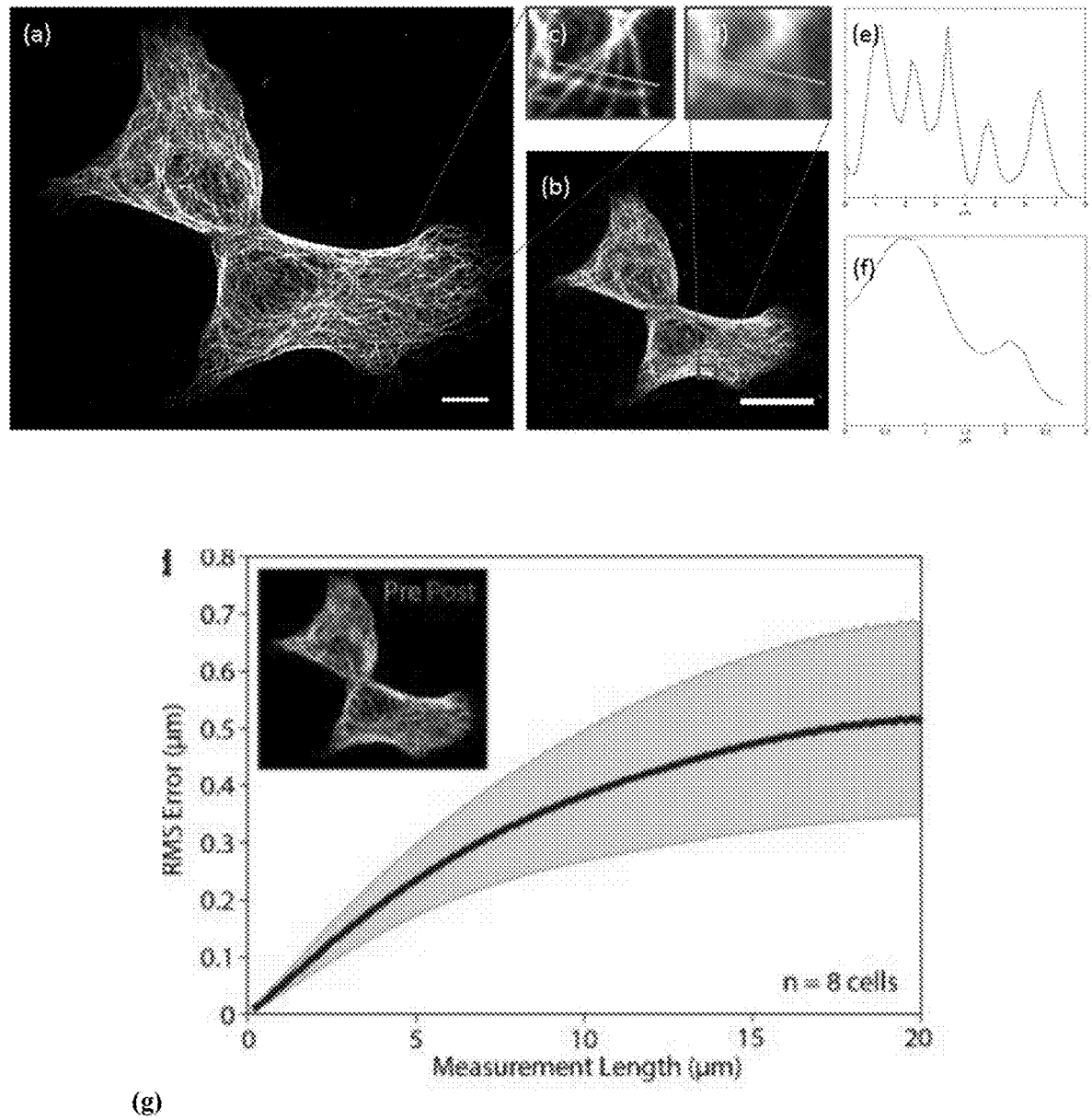
FIG. 6A-6G: In situ synthesis and expansion of cultured cells with tetragel. (a, c) Fluorescence image of expanded HEK 293 cells immunostained with anti-α-tubulin primary antibodies and dye-conjugated secondary antibodies. Scale bar, 20 µm. (b, d) Fluorescence image of the same cells before expansion. Scale bar, 20 µm. (e) Line profile of the image specified by the solid line in (c). (f) Line profile of the image specified by the solid line in (d). (g) RMS error curve for the HEK293 cell expansion (blue line, mean; shaded area, standard deviation; n=8 cells). Inset, non-rigidly registered and overlaid pre-expansion (green) and post-expansion (magenta) images used for the RMS error estimation.

FIG. 5 demonstrates an implementation of such anchoring. Yellow fluorescent proteins (YFPs) in a Thy1-YFP mouse brain slice are retained by a small-molecular linker, NHS-azide. The YFP molecules were first reacted with NHS-azide and then anchored to the hydrogel by click-reaction. The gel was expanded and immunostained by antibodies (anti-GFP) post-expansion for visualization. FIG. 6 shows expansion of antibody-stained HEK cells using the tetragel. The dye-conjugated secondary antibodies are anchored to the tetragel by NHS-azide. Other molecules such as RNAs and lipids, for example, can be similarly anchored to the gel through similarly designed small-molecule linkers.

Figures 7A, 7B, 7C:
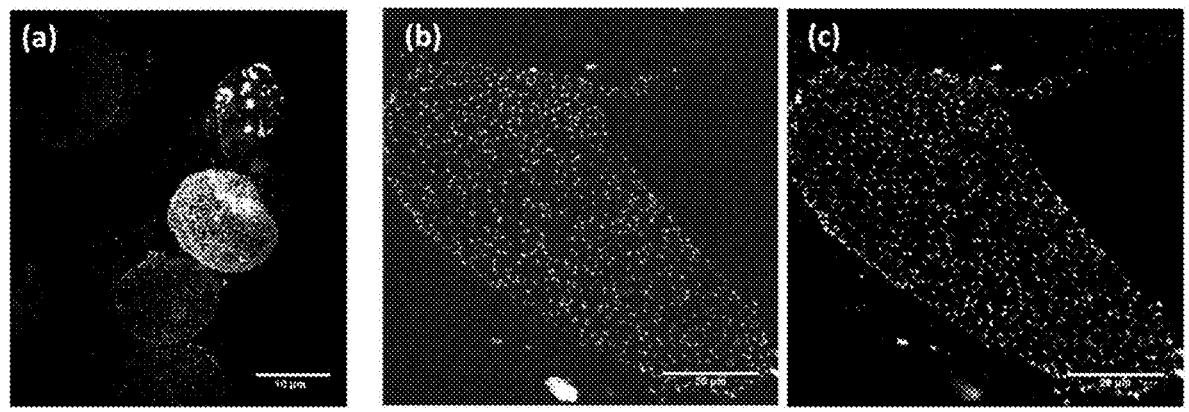
FIG. 7A-7C: In situ synthesis and expansion of nuclear pore complex with tetragel. (a) Pre-expansion live fluorescent image of nuclear pore complex with GFP fusion. Scale bar, 10 µm. (b), (c) Post-expansion fluorescent image of (b) GFP and (c) Cy3-conjugated secondary antibody (Nup133 primary antibody). Scale bars, 20 µm.

In another implementation, both GFP and Cy3-conjugated secondary antibodies are linked into the tetragel using NHS-azide. FIG. 7 shows pre- and post-expansion images of nuclear pore complex with simultaneous GFP labeling and antibody staining.

In some embodiments, after the sample has been anchored to the swellable hydrogel, the sample is, optionally, subjected to a disruption of the endogenous biological molecules or the physical structure of the biological sample, leaving the linkers intact and anchored to the swellable material. In this way, the mechanical properties of the sample-swellable material complex are rendered more spatially uniform, allowing isotropic expansion with minimal artifacts.

As used herein, the "disruption of the endogenous physical structure of the sample" or the "disruption of the endogenous biological molecules" of the biological sample generally refers to the mechanical, physical, chemical, biochemical or, enzymatic digestion, disruption or break up of the sample so that it will not resist expansion. In one embodiment, a protease enzyme is used to homogenize the sample-hydrogel complex. It is preferable that the disruption does not impact the structure of the hydrogel but disrupts the structure of the sample. Thus, the sample disruption should be substantially inert to the hydrogel. The degree of digestion can be sufficient to compromise the integrity of the mechanical structure of the sample or it can be complete to the extent that the sample-hydrogel complex is rendered substantially free of the sample. In one embodiment, the disruption of the physical structure of the sample is protein digestion of the proteins contained in the biological sample. The sample-hydrogel complex is then isoptropically expanded. In one embodiment, a solvent or liquid is added to the complex which is then absorbed by the hydrogel and causes swelling. Where the hydrogel is water swellable, an aqueous solution can be used.

As described herein, the expanded and/or labelled sample can be viewed using microscopy. The sample can be imaged using an optical microscope, allowing effective imaging of features below the classical diffraction limit. Where the resultant specimen is transparent, custom microscopes capable of large volume, widefield of view, 3D scanning can also be used in conjunction with the expanded sample.

In one embodiment, the addition of water an aqueous solution allows for the embedded sample to expand relative to its original size in three-dimensions. Thus, the sample can be increased 100-fold or more in volume. This is because the polymer is embedded throughout the sample, therefore, as the polymer swells (grows) it expands the tissue as well. Thus, the tissue sample itself becomes bigger. As the material swells isotropically, the anchored tags maintain their relative spatial relationship.

Figures 8A, 8B:
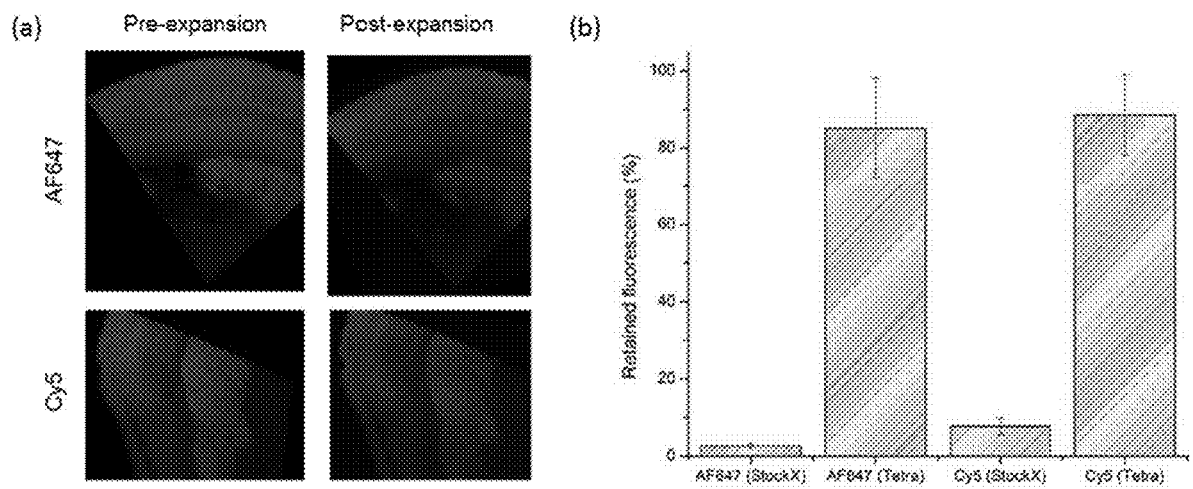
FIGS. 8A and 8B: Retention of far-red dye in tetragel. (a) Fluorescence images of mouse brain slices stained with far-red dyes before and after expansion with tetragel. The brain slices were immunostained with Tom 20 primary antibodies and far-red dye conjugated secondary antibodies. (b) Retention of far-red dyes (Alexa Fluor 647 (AF647) and Cyanine 5 (Cy5)) with Stock X gel (used for conventional ExM) and tetragel.

Use of the tetragel system, as described here, for ExM may eliminate radicals during the in situ polymerization. In radical polymerization, radical species are known to damage organic molecules such as fluorescent dyes and tags in biological samples (e.g., molecules that have C—C double bonds). As described, tetragels are formed by linking monomers with a non-radical, bio-orthogonal reaction. Therefore, the hydrogel formation introduces much less chemical damage to biomolecules and tags, reserving the chemical structures as well as increasing the retention after expansion. For example, the C—C double bonds present in some of the far-red dyes can be robustly retained after gelation and expansion with tetragel (FIG. 8).

In addition to a single round of expansion, the hydrogels described herein can be used in the iterative ExM (iExM) process. The process of iteratively expanding the samples can be applied to samples that have been already expanded using the techniques described herein one or more additional times to iteratively expand them such that, for example, a 5-fold expanded sample can be expanded again 3- to 4-fold, resulting in as much as a 17- to 19-fold or more linear expansion. The iExM procedure begins with first conducting ExM on a sample and further provides one or more additional and iterative expansions of the sample by forming, for example, another hydrogel inside an expanded hydrogel such as the first expanded hydrogel of the ExM method. The iterative ExM methods of the present claims comprising using the hydrogel described herein (formed by the reaction of a monomer of Formula (A) with a monomer of Formula (B1) or (B2) for any steps including the first gel, the second gel, or both first and the second gel.

In one embodiment, in iExM, the first swellable material and the non-swelling material are made with a different crosslinker compared to the second swellable material in order to selectively digest the first swellable material and the non-swellable re-embedding material while the second swellable material remains intact. Selective digestions of each successive swellable material depends on the conditions under which the cross-linkers of the target swellable material cleavable. For example, swellable materials cross-linked with DHEBA, may be cleaved and dissolved by treatment with 0.2M sodium hydroxide for 1 hour. Swellable materials made with BAC can be dissolved and the cross-linker cleaved by treatment with Tris(2-carboxyethyl)phosphine hydrochloride (TCEP).

In some embodiments, the method comprises:
a) permeating a biological sample with a first hydrogel, wherein the sample is anchored to the hydrogel;
b) swelling the first hydrogel resulting in a first expanded sample;
c) permeating the first expanded sample with a second hydrogel; and
d) swelling the second hydrogel resulting in a second expanded sample;
wherein the first hydrogel and/or the second hydrogel is the product a non-radical polymerization reaction between a monomer of Formula (A) and a monomer of Formula (B1) or (B2).

In some embodiments, the invention provides method for enlarging a sample of interest for microscopy, the method comprising the steps of:
a) embedding a sample in a first hydrogel;
b) swelling the first hydrogel to form a first enlarged sample;
c) re-embedding the first enlarged sample in a non-swellable material;
d) embedding the first enlarged sample in a second hydrogel; and
e) swelling the second hydrogel to form a second enlarged sample that is enlarged as compared to the first enlarged sample;
wherein the first hydrogel and/or the second hydrogel is the product a non-radical polymerization reaction between a monomer of Formula (A) and a monomer of Formula (B1) or (B2).

The term "re-embedding" comprises permeating (such as, perfusing, infusing, soaking, adding or other intermixing) the sample with a swellable or non-swellable material, preferably by adding precursors thereof. Alternatively or additionally, embedding the sample in a non-swellable material comprises permeating one or more monomers or other precursors throughout the sample and polymerizing the monomers or precursors to form the non-swellable material or polymer. In this manner, the first enlarged sample, for example, is embedded in the non-swellable material. Embedding the expanded sample in a non-swellable material prevents conformational changes during sequencing despite salt concentration variation. The non-swellable material can be charge-neutral hydrogels. For example, it can be polyacrylamide hydrogel, composed of acrylamide monomers, bisacrylamide crosslinker, ammonium persulfate (APS) initiator and tetramethylethylenediamine (TEMED) accelerator.

In one embodiment, the cleavable version of the tetragel (e.g., Monomer A in FIG. 2B; Monomer B in FIG. 3A) can be used as the first gel for iExM. After gelation, the cleavable tetragel can be then reembedded, gelled and then cleaved for the $2^{nd}$ round of expansion. In this iExM process, the linker may have a functional group that can be anchored to the tetragel, such as a DBCO or azide group.

In one embodiment, the biological sample and each enlarged sample thereafter is permeated with one or more monomers or a solution comprising one or more monomers or precursors which are then reacted to form a swellable or non-swellable polymerized gel depending on what step of the method is being performed. For example, if the biological sample is to be embedded in hydrogel AB2, a solution comprising the monomer of Formula (A) and a monomer of Formula (B2) can be perfused throughout the sample.

The invention also includes a method for preparing and amplifying nucleic acids in situ and methods for in-situ sequencing of target nucleic acids in an expanded composite comprising biological sample and a hydrogel as described herein. Methods of preparing and amplifying nucleic acids and sequencing using expanded or enlarged composites ("expansion sequencing" or "ExSEQ") have been described, for example, in U.S. Pat. App. Pub. No. 2016/0304952 and U.S. patent application Ser. No. 15/789,419, the contents of which are expressly incorporated by reference herein. Expanding specimens before sequencing separates sequencing targets by a programmable volumetric factor, enabling detection of multiple species within a diffraction-limited spot in a pre-expansion space, using diffraction limited microscopy in a post-expansion space. In addition, expansion results in homogenization of the chemical environment (which is ~99% water throughout the specimen in the expanded state) and providing optical clarity. In certain aspects, the method comprises the steps of:
a. attaching target nucleic acids present in the sample with a bifunctional crosslinker;
b. permeating the sample with a monomer of Formula (A) and a monomer of Formula (B1) or (B2) under conditions suitable to form a hydrogel by non-radical polymerization and thereby forming a sample—hydrogel complex, wherein the bifunctional crosslinker is attached both to the target nucleic acids present in the sample and to the hydrogel;
c. digesting proteins present in the sample; and
d. expanding the complex to form a first enlarged composite.

In one embodiment, the method further comprises re-embedding the first enlarged sample in a non-swellable material to form a re-embedded sample.

In one embodiment, the method further comprises modifying the target nucleic acids or the nucleic acid adaptor to form a target nucleic acids or a nucleic acid adaptor useful for sequencing. In this manner, the nucleic acids present in the re-embedded composite may be sequenced.

"Modifying the target nucleic acids or the nucleic acid adapter" can, for example, refer to biochemical modification, for example, contacting the target nucleic acids or the nucleic acid adapter with reverse transcriptase. In certain examples, the nucleic acid adaptors are attached to target nucleic acids via ligation to the target nucleic acid. In one embodiment, the nucleic acid adaptors are attached to target nucleic acids via a chemical reagent capable of reacting with amine groups on the target nucleic acid.

The term "nucleic acid" and "polynucleotide" are used interchangeably herein to refer to a polymer having multiple nucleotide monomers. A nucleic acid can be single- or double-stranded, and can be DNA (e.g., cDNA or genomic DNA), RNA, or hybrid polymers (e.g., DNA/RNA). Nucleic acids can be chemically or biochemically modified and/or can contain non-natural or derivatized nucleotide bases. "Nucleic acid" does not refer to any particular length of polymer e.g., greater than about 2 bases, greater than about 10 bases, greater than about 100 bases, greater than about 500 bases, greater than 1000 bases, greater than 10,000 bases, greater than 100,000 bases, greater than about 1,000,000, up to about $10^{10}$ or more bases composed of nucleotides. Additionally, a polynucleotide can be native to the sample (for example, present in the sample at the time the sample is obtained from the original organism). Alternatively, a polynucleotide can be artificial or synthetic, such as when the polynucleotide is added to the sample to cause hybridization to a target nucleic acid. The term "polynucleotide" is intended to include polynucleotides comprising naturally occurring nucleotides and/or non-naturally occurring nucleotides. Non-naturally occurring nucleotides can include chemical modifications of natural nucleotides. In this case, it is preferred that the synthetic polynucleotides can hybridize to the tagged genomic fragments.

The term "sequence," in reference to a nucleic acid, refers to a contiguous series of nucleotides that are joined by covalent bonds (e.g., phosphodiester bonds).

The term "target nucleic acid" refers to a nucleic acid whose presence in a sample may be identified and sequenced. A target nucleic acid can be any nucleic to be selected and, optionally, amplified or sequenced preferably in combination with the nucleic acid adaptor. Target nucleic acids for use in the provided methods may be obtained from any biological sample using known, routine methods.

In one embodiment, the method further comprises the step of passivating the first swellable material. As used herein the term "gel passivation" refers to the process for rendering a gel less reactive with the components contained within the gel such as by functionalizing the gel with chemical reagents to neutralize charges within the gel. For example, the carboxylic groups of sodium acrylate, which may be used in the swellable gel, can inhibit downstream enzymatic reactions. Treating the swellable gel composed of sodium acrylate with 1-Ethyl-3-(3-dimethylaminopropyl)carbodiimide (EDC) and N-Hydroxysuccinimide (NHS) allows primary amines to covalently bind the carboxylic groups to form charge neutral amides and passivate the swellable gel. After re-embedding in the non-swellable gel, the swellable gel may also be partially or completely degraded chemically, provided that the target nucleic acids can either stay anchored or can be transferred to the non-swellable gel.

As described above, the biological sample can be labelled or tagged, for example, with a detectable label. Also as described above, the biological sample can be treated with a detergent prior to being contacted with the hydrogel precursor(s).

In accordance with the invention, chemically fixed and permeabilized biological specimens are expanded. The expanded gel may be converted to a non-expanding state, by re-embedding in a non-expanding material. RNA or DNA molecules present in the sample may be sequenced using methods known to those familiar with the art, including sequencing by hybridization, ligation, and synthesis. Sequencing can be carried out by any method known in the art including, but not limited to, sequencing by hybridization, sequencing by ligation or sequencing by synthesis. General sequencing methods known in the art, such as sequencing by extension with reversible terminators, fluorescent in situ sequencing (FISSEQ), pyrosequencing, massively parallel signature sequencing (MPSS) and the like are suitable for use in the methods of the invention. Reversible termination methods use step-wise sequencing-by-synthesis biochemistry that coupled with reversible termination and removable fluorescence.

FISSEQ is a method whereby DNA is extended by adding a single type of fluorescently labelled nucleotide triphosphate to the reaction; washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described, for example in, (Lee et al., Science. 343, 1360-3 (2014).

Pyrosequencing is a method in which the pyrophosphate (PPi) released during each nucleotide incorporation event (i.e., when a nucleotide is added to a growing polynucleotide sequence). The PPi released in the DNA polymerase-catalyzed reaction is detected by ATP sulfurylase and luciferase in a coupled reaction which can be visibly detected. The added nucleotides are continuously degraded by a nucleotide-degrading enzyme. After the first added nucleotide has been degraded, the next nucleotide can be added. As this procedure is repeated, longer stretches of the template sequence are deduced. Pyrosequencing is described further in Ronaghi et al. (1998) Science 281:363.

MPSS utilizes ligation-based DNA sequencing simultaneously. A mixture of labelled adaptors comprising all possible overhangs is annealed to a target sequence of four nucleotides. The label is detected upon successful ligation of an adaptor. A restriction enzyme is then used to cleave the DNA template to expose the next four bases. MPSS is described further in Brenner et al., (2000) Nat. Biotech. 18: 630.

The invention is illustrated by the following examples which are not meant to be limiting in any way.

EXEMPLIFICATION

Materials and Methods

I. Synthesis of Monomer A

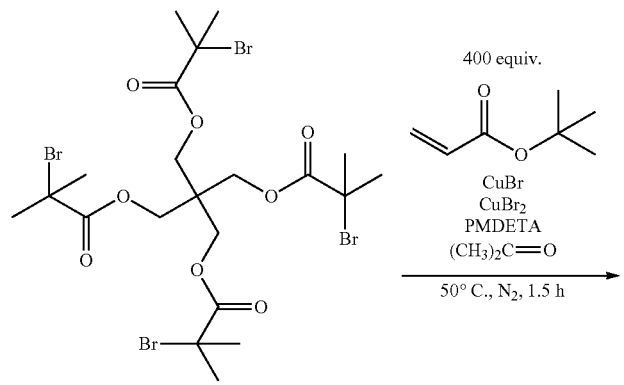

-continued
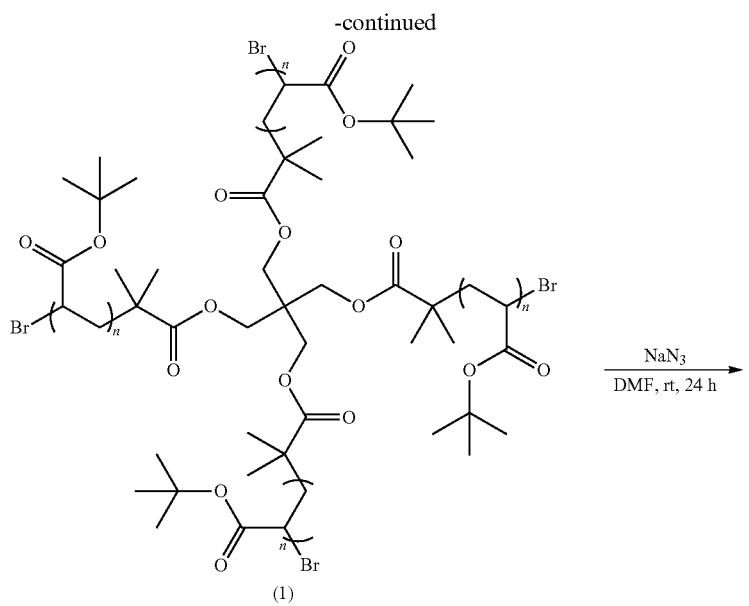
(1)
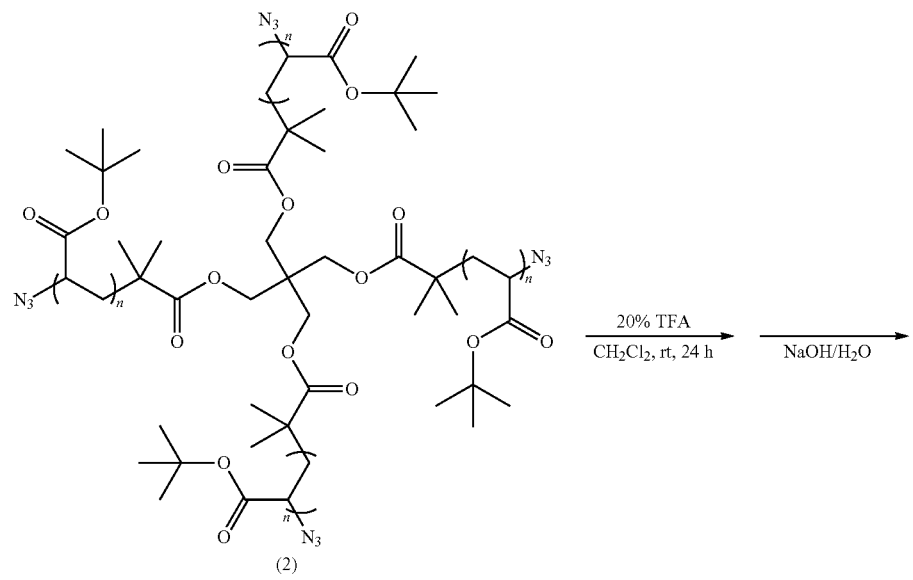
(2)

-continued

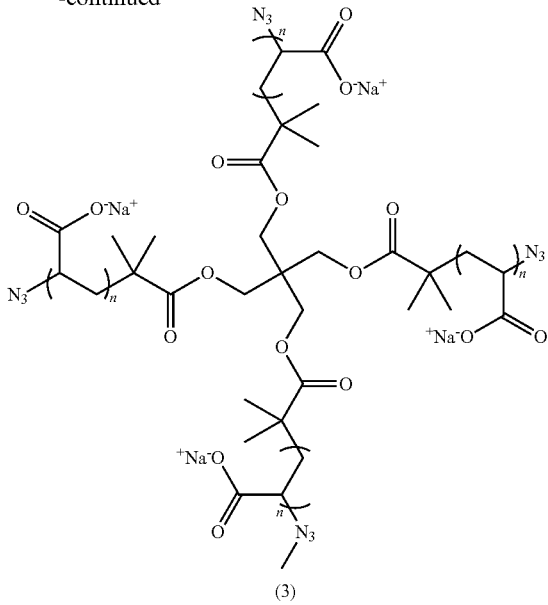

(3)

Synthesis of Br-Terminated Monomer (1):

Synthesis of (1) was carried out with a modified procedure of as described in Oshima et al. Before use, t-butyl acrylate was purified with an inhibitor removal column to remove trace amounts of 4-methoxyphenol. To 640 mg of CuBr and 48 mg of $CuBr_2$ was added 128 mL of t-butyl acrylate, and the mixture was bubbled with dry nitrogen at 50° C. A total of 1.03 mL of PMDETA was then added dropwise. After 5-10 min, a solution of 1.6 g of star core (pentaerythritol tetrakis(2-bromoisobutyrate)) dissolved in 16 mL acetone was added dropwise. The reaction was carried out for 90 min at 50° C., with dry nitrogen bubbling for the first ~10 min. Unreacted t-butyl acrylate was then removed by rotary evaporation. The crude product mix was then dissolved in DMF and precipitated with water. Precipitation was repeated an additional two times, yielding 15.3 g of a white powder.

Synthesis of $N_3$-Terminated Monomer (2):

A total of 15.3 g of Br-terminated monomer (1) was dissolved in 80 mL of DMF. Excess sodium azide (exceeding its solubility limit in DMF) was added to the mixture, and the reaction was carried out overnight at room temperature. The supernatant was subsequently decanted and precipitated with water, yielding 11 g of a white powder.

Synthesis of Deprotected Monomer (3):

A total of 5.04 g of (2) was dissolved in 30 mL of $CH_2Cl_2$, followed by addition of 15 mL of trifluoroacetic acid. The reaction was carried out at 4° C., resulting the gradual precipitation of a white powder. After 24-48 h, the product was collected by centrifugation, washed with acetone, and dried in a low-humidity chamber. The product was re-suspended in a solution of $NaOH/H_2O$ to a final concentration of 200 mg/mL and pH 7.

Monomer (3) is referred to as "monomer 1" in the section below.

2. Synthesis of Monomer B

Amine-terminated PEG monomer (10 kDa; purchased from NOF) was dissolved in DMSO to a concentration of 100-200 mg/mL. BCN—NHS, DBCO—NHS or DBCO-sulfo-NHS (referred to as Monomer B as well as monomers 2, 2', and 2", respectively, below) (1:1 molar ratio to amines) was then added to the solution. The conjugation reaction was carried out overnight. The product solution was used for gelation reactions without further work-up.

3. Gelation

Cultured cells and brain slices were fixed and immunostained as previously described in Tillberg et. al. Unless otherwise noted, single-round expansion of cells and tissues were carried out using the subsequent standard gelation protocol. Fixed biological samples were soaked in 0.1 mg/mL NHS-azide in 1× PBS overnight and washed with 1× PBS twice immediately before the gelation.

Monomer A and Monomer B solutions were mixed with a 1:1 molar ratio and additional water was added to a final concentration of ~3.3 wt % for Monomer A to yield the gelling solution. In a typical implementation, 10 uL of Monomer A (200 mg/mL), 10 uL of Monomer B (200 mg/mL), and 40 ul of water were mixed and vortexed to give the gelling solution. The samples were gelled in the gelling solution at 4° C. for 8 hours. For example, 10 μL of monomer 1 (200 mg/mL), 10 μL of monomer 2 (200 mg/mL), and 40 μl of water were mixed. After applying the gelling solution to the samples in the gelation chamber as previously described, gelation was carried out overnight at 4° C. The amount of monomers 1 and 2 (or 2', 2") and the mixed gelling solution was scaled up and down proportionally according to the size and number of the samples.

4. Digestion and Expansion

Gelled samples were digested overnight in digestion buffer with proteinase K (8 units/mL) as described in Tillberg, et. al. The samples were washed in excessive amount of water 3 times for 20 min each time for the expansion.

For fluorescein visualization of tetragels (TGs) (FIGS. 4-6 and 8-9), a trace amount of fluorescein amine was mixed in the gelling solution before gelation for 1-2 hours at 37° C. Briefly, a stock solution of ~50 mM fluorescein-azide was prepared by adding 5 μL of 100 mM fluorescein-amine in DMSO to 5 μL of 20 mg/mL NHS-azide in DMSO. ~3 μL of the fluorescein-azide stock solution was then added to ~60 μL of the gelling solution (with monomers 2 or 2' or 2") before gelation in circular molds of ~3 mm diameters.

5. Imaging

All samples were imaged with an Andor spinning disk (CSU-W1 Yokogawa) confocal system on a Nikon Eclipse Ti-E microscope body or a Nikon Eclipse Ti-E widefield microscope. High resolution images were collected on the spinning disk confocal system using a CFI Apo LambdaS LWD 40×, 1.15 NA water-immersion objective.

6. HeLa Cell Culture. HeLa Cell Expansion (Post-Expansion Staining and Multi-Round Iterative Expansion).

High-Temperature Treatment for Post-Gelation Antibody Staining

After gelation, sample chambers were gently opened with a razor blade. Empty gels surrounding the circular coverslips containing HeLa cultures were trimmed away. Circular coverslips were placed into autoclave-safe glass vials containing 1 mL of 1× PBS+1M NaCl, and incubated at RT for 30 min. Samples were incubated in MAP Buffer (200 mM SDS+200 mM NaCl+50 mM Tris, pH to 9.0) overnight at 37° C., followed by a 3 hr incubation at 70° C. and 1 hr incubation at 95° C. Following the high-temperature treatment, samples were cooled to RT and washed 4 times in PBST (1× PBS+0.1% Triton X-100) for 30 min each. Samples were stained sequentially with sheep anti-tubulin primary antibody and anti-sheep secondary antibody. Each staining step was performed in PBST at RT with overnight incubation, followed by 3 washes in PBST for 1 hr each.

7. HSV-1 Virion Expansion (Direct Labeling and Multi-Round Iterative Expansion)

Immobilization and Fixation

Purified HSV-1 virion stock was prepared by the Viral Core Facility at the Massachusetts General Hospital (MGH) as previously described. The HSV stock was diluted to a functional titer of $2.5 \times 10^8$ functional virions/mL in PBS and kept on ice until immobilization. A #0 circular 12-mm coverslip was treated with oxygen plasma for 1 min. Immediately after the treatment, 30 uL of the diluted HSV-1 solution was drop-casted to the coverslip and incubated for 15 min at room temperature. The immobilized viruses were fixed in PBS+4% PFA for 10 min, and then washed with PBS twice, each time for 5 min.

Oligo Conjugation to Envelope Proteins

Envelope proteins on the fixed viruses were conjugated to a DNA oligo with the SoluLink bioconjugation chemistry as previously described. The oligo provided a molecular handle for signal anchoring, transfer and amplification through the iterative expansion process. Briefly, a 19-bp oligo (sequence B1') with a 5' amine modification (Integrated DNA Technologies) was purified with ethanol precipitation and reacted with Sulfo-S-4FB overnight in Buffer A (150 mM NaCl, 100 mM $Na_2HPO_4$, pH 7.4) at a molar ratio of 1:15. The S4FB-reacted oligo was purified with a size exclusion filter, and then stored at 4° C. Fixed viruses immobilized on the coverslip were washed in Buffer A for 5 min, and then incubated with 100 uL of 160 mM of S-HyNic in Buffer A for 2 hours at room temperature. The S-HyNic-reacted viruses were washed with Buffer C (150 mM NaCl, 100 mM $Na_2HPO_4$, pH 6.0) twice, each time for 5 min. Oligo conjugation solution was prepared by first adding 50 nmol of purified S4FB-reacted oligo to 100 uL of Buffer C, and then adding an amount of 10× TurboLink Catalyst Buffer that equals to ⅑ of the combined volume. The S-HyNic-reacted viruses were incubated in the oligo conjugation buffer overnight at room temperature in a humidified chamber. Finally, the oligo-conjugated viruses were washed 3 times with PBS, each time for 10 min, and then incubated in detergent-free hybridization buffer (10% Dextran sulfate, 1 mg/mL yeast tRNA, 5% NDS, 2×SSC) for 3 hours at room temperature. Viruses were incubated with 4 nmol of oligo B1-acrydite or oligo B1-azide (for PAA or TG, respectively) in 300 uL of detergent-free hybridization buffer, overnight at room temperature, and then washed 3 times in PBS, each time for 10 min.

Gelation and Digestion

As described in the previous section, cleavable TG gelling solution was prepared by mixing monomer 1 (200 mg/mL) and monomer 2" (200 mg/mL) at a molar ratio of ~1:1 and adding water to adjust the final concentration of monomer 1 to ~3.3% (w/v). BAC-crosslinked cleavable PAA gelling solution was prepared as previously described. A gelation chamber was constructed around the virus-immobilized coverslip by the following steps. First, the coverslip was transferred to the center of a glass slide. Spacers consisting of a stack of a #0 and a #1 coverslip were placed on either side of the virus-immobilized coverslip. 50 uL of freshly prepared TG or PAA gelling solution was added to the coverslip, and the chamber was closed by placing a rectangular coverslip on top of the spacers. The gelling solution was further added from the side of the chamber until the chamber was completely filled. The gelation chambers were incubated for 2 hours at 37° C. After gelation, the chambers were partially opened using a diamond scribe to remove portions of the top cover glass that were not directly above the virus-immobilized coverslip. The chambers were then placed into a rectangular 4-well dish and incubated in digestion buffer with Proteinase K at 8 U/mL (New England Bio Labs; 1:100 dilution) overnight at room temperature with gentle shaking. After digestion, the top cover glass was removed. The diameter of the indentation casted by the circular 12-mm coverslip was measured for downstream estimation of the overall expansion factor. Regions inside of the circular 12-mm coverslip (i.e. regions with the immobilized viruses) were trimmed into a parallelogram, whose shape can be used to indicate the side of the gel that the viruses were located. The side lengths of the parallelogram were measured. Finally, trimmed gels were washed twice in PBS, each time for 10 min. To de-hybridize B1' and B1 oligos, the gels were incubated in 80% formamide at room temperature with gentle shaking, and then washed 3 times in PBS, each time for 10 min.

Re-Embedding Into a BAC-Crosslinked Non-Expanding $2^{nd}$ Gel

The gels were transferred (with the virus side down, as deduced from the shape of the parallelogram) into a rectangular 4-well dish that carries a glass slide in each well, and expanded in water 3 times, each time for 30 min. Gels were then incubated in 3 mL of BAC non-expanding gelling solution (10% acrylamide, 0.2% BAC, 0.05% TEMED, 0.05% APS) for 5 min with gentle shaking. After the incubation, the non-expanding gelling solution was removed from the well, and the glass slide carrying the expanded gel was transferred to a gelation chamber. Spaces consisting of a stack of #1.5 cover glasses were placed on either side of the gel, and the chamber was closed with a rectangular cover glass. The non-expanding gelling solution was added from the side of the chamber until the chamber was completely filled. The gelation chambers were incubated for 2 hours at 37° C. After gelation, the chambers were opened by removing the top cover glass. Side lengths of the parallelogram were measured. The gels were trimmed to leave only the portion inside the parallelogram, while preserving the shape of the parallelogram. Side lengths of the trimmed gels were measured. Finally, the trimmed gels were washed twice in PBS, each time for 10 min.

1st Linker Hybridization

The gels were incubated in hybridization buffer (4×SSC+20% formamide) for 30 min at room temperature. For readout after 2-round expansion (~10-20× expansion factor), the gels were incubated with 1 nmol of oligo 5'Ac-B1'-4xB2' in 500 uL of hybridization buffer overnight at room temperature. For readout after 3-round expansion (~40-80× expansion factor), the gels were incubated with 1 nmol of oligo 5'Ac-B1'-A2' in 500 uL of hybridization buffer overnight at room temperature. After incubation, the gels were washed in hybridization buffer 3 times, each time for 1 hour, and then overnight, all with gentle shaking. The gels were then washed 3 times in PBS, each time for 5 min.

Re-Embedding Into a DATD-Crosslinked Expanding $3^{rd}$ Gel

The gels were incubated in DATD expanding gelling solution (7.5% sodium acrylate, 2.5% acrylamide, 0.5% DATD, PBS, 2M NaCl, 0.01% 4-HT, 0.2% TEMED, 0.2% APS) for 30 min at 4° C. The gels (with the virus side down) were enclosed in gelation chambers, incubated for 2 hours at 37° C., size-measured, trimmed, size-re-measured, and washed as described in "Re-embedding into a BAC-crosslinked non-expanding $2^{nd}$ gel".

Cleaving BAC-Crosslinked $1^{st\ and}\ 2^{nd}$ Gels

The gels were incubated in BAC-cleaving buffer (0.25M TCEP-HCl, 0.75M Tris-HCl, pH 8.0) overnight at room temperature. The gels were then washed 4 times in PBS, each time for 30 min. For samples designated for 3-round expansion, the gels were incubated in thiol-blocking buffer (100 mM maleimide, 100 mM MOPS, pH 7.0) for 2 hours at room temperature. The thiol-blocked gels were washed 3 times in PBS, each time for 10 min.

LNA Hybridization for Readout After 2-Round Expansion

For samples designated for 2-round expansion, the gels were incubated with 1 nmol of LNA_B2-Atto647N in 500 uL of hybridization buffer. The LNA-hybridized gels were washed in hybridization buffer 3 times, each time for 1 hour, and then overnight, all with gentle shaking. The gels were then washed 3 times in PBS, each time for 5 min.

Gel Expansion, Immobilization, and Imaging for 2-Round Expanded Samples

The gels were trimmed into smaller pieces (~5×5 mm) while preserving the shape of the parallelogram. First, the gels were transferred (with the virus side down, as deduced from the shape of the parallelogram) into a rectangular 4-well dish that carries a glass slide in each well, and expanded in water 3 times, each time for 30 min. Wells in a glass-bottom 6-well plate were modified with poly-lysine as previously described. The expanded gels were then gently transferred to the poly-lysine modified glass-bottom plate for imaging as previously described.

Re-Embedding into a DATD-Crosslinked Non-Expanding $4^{th}$ Gel (for 3-round expansion)

Thiol-blocked gels in "Cleaving BAC-crosslinked $1^{st}$ and $2^{nd}$ gels" were subsequently trimmed into smaller pieces (~5×5 mm) while preserving the shape of the parallelogram. The gels were transferred (with the virus side down, as deduced from the shape of the parallelogram) into a rectangular 4-well dish that carries a glass slide in each well, and expanded in water 3 times, each time for 30 min. The gels were transferred onto a slide glass and trimmed in the z-direction into a thickness of 1 mm. Briefly, the glass slide (with 1-mm thickness) carrying the expanded sample was placed between two stacks of 1-mm-glass slides, and a cryostat blade was pushed slowly through the expanded gel. The bottom gel, which carries the virus at the bottom side, was transferred back to the 4-well plate. The z-trimmed gels were then incubated in DATD non-expanding gelling solution (10% acrylamide, 0.5% DATD, 0.05% TEMED, 0.05% APS) for 30 min at 4° C. The gels were enclosed in gelation chambers, incubated for 2 hours at 37° C., size-measured, trimmed, size-re-measured, and washed as described in "Re-embedding into a BAC-crosslinked non-expanding $2^{nd}$ gel".

$2^{nd}$ Linker Hybridization

The gels were incubated in hybridization buffer (4×SSC+20% formamide) for 30 min at room temperature. The gels were incubated with 0.5 nmol of oligo 5'Ac-A2-4xB2' in 1 mL of hybridization buffer overnight at room temperature. After incubation, gels were washed in hybridization buffer 3 times, each time for 1 hour, and then overnight, all with gentle shaking. The gels were then washed 2 times in PBS, each time for 30 min.

Re-Embedding Into a Bis-Crosslinked Expanding $5^{th}$ Gel

The gels were incubated in bis expanding gelling solution (7.5% sodium acrylate, 2.5% acrylamide, 0.15% bis, PBS, 2M NaCl, 0.01% 4-HT, 0.2% TEMED, 0.2% APS) for 30 min at 4° C. The gels (with the virus side down) were enclosed in gelation chambers, incubated for 2 hours at 37° C., size-measured, trimmed, size-re-measured, and washed in the same way as described in "Re-embedding into a BAC-crosslinked non-expanding $2^{nd}$ gel".

Cleaving DATD-Crosslinked $4^{th}$ and $5^{th}$ Gels

The gels were incubated in DATD-cleaving buffer (20 mM sodium periodate, PBS, pH 5.5) for 30 min at room temperature. The gels were then washed 3 times in PBS, each time for 30 min, and then overnight with gentle shaking.

LNA Hybridization for Readout After 3-Round Expansion

The gels were hybridized with LNA_B1_Atto647N as described in "LNA hybridization for readout after 2-round expansion".

Gel Expansion, Immobilization, and Imaging

The gels were trimmed, expanded, immobilized and imaged as described in "Gel expansion, immobilization, and imaging for 2-round expanded samples".

Expansion Factor Estimation

Side lengths of the gels were recorded before and after each trimming step (for example, after every re-embedding step and before every immobilization step) and immediately before imaging. Single-stage expansion factor was calculated by taking the average quotient between the pre-trimming size of the current step and the post-trimming size of the previous step. Overall expansion factor was calculated from the product of all the previous single-step expansion factors till a specific step.

HSV-1 Virion Diameter Analysis.

Diameters of the HSV-1 virion envelope protein layer were measured with a semi-automated analysis pipeline implemented on MATLAB ("Particle Analysis Assistant"). The MATLAB code for "Particle Analysis Assistant" is available for download. Briefly, within an acquired image z-stack, all round objects with a local minimum inside the object were identified as the virions and were analyzed. First, the center of each virion was determined manually within the image z-slice that had the largest virion diameter. Next, the line profile of the virion was automatically measured across the virion center along the x-axis and the distance between the two local maxima in the line profile was recorded as the virion diameter (along the x-axis). When the automated diameter measurement failed due to fluorescent signals from adjacent virions or unspecific fluorescent label readouts, manual correction of the peak locations was performed. Virions with repeated measurement failures were manually rejected from the final statistics. Student's twotailed t-test was used to determine the statistical significance between the mean diameters derived from the TG- and PAA-based iteratively expanded HSV-1 virions.

Averaged Single Particle Images of HSV-1 Virions.

Single HSV-1 virion particle images were generated using a semi-automated analysis pipeline implemented on MATLAB ("Particle Analysis Assistant"). First, the center of the virions in the previous diameter analysis was inspected and re-aligned manually. During the inspection, a small portion (<10%) of the virions, which had significant overlaps with the neighboring virions, were rejected for averaging. Next, the single virion image around each virion center was automatically cropped, calibrated with the expansion factor, and then averaged.

TABLE 1

DNA oligo sequences.

| Oligo Name | Purpose | Sequence (IDT format) | SEQ ID NO | Modification |
|---|---|---|---|---|
| 5'Amine-B1' | Pre-G1 conjugation to envelope proteins | AAT ACG CCC TAA GAA TCC GAA C | 1 | 5' Amino Modifier C6 |
| 5'Acrydite-B1 | Pre-G1 adaptor for PAA-based iExM | GTT CGG ATT CTT AGG GCG TA | 2 | 5' Acrydite |
| 3'Azide-B1 | Pre-G1 adaptor for TG-based iExM | GTT CGG ATT CTT AGG GCG TA | 3 | 3' Azide |
| 5'Acrydite-B1'-4xB2' | Post-G2 linker for 2-round iExM | TAC GCC CTA AGA ATC CGA ACA TGC ATT ACA GCC CTC AAT GCA TTA CAG CCC TCA ATG CAT TAC AGC CCT CAA TGC ATT ACA GCC CTC A | 4 | 5' Acrydite |
| 5'Acrydite-B1'-A2' | Post-G2 linker for 3-round iExM | TAC GCC CTA AGA ATC CGA ACA TGG TGA CAG GCA TCT CAA TCT | 5 | 5' Acrydite |
| 5'Acrydite-A2-4xB2' | Post-G4 linker for 3-round iExM | AGA TTG AGA TGC CTG TCA CCA TGC ATT ACA GCC CTC AAT GCA TTA CAG CCC TCA ATG CAT TAC AGC CCT CAA TGC ATT ACA GCC CTC A | 6 | 5' Acrydite |
| LNA_B2-Atto647N | Post-G3 or Post-G5 readout | TGAGGGCTGTAATGC | 7 | 3' Atto 647N, LNAs (underlined) |

TABLE 2

Recipes of hydrogel gelling solutions.

| Gel Name | Purpose | Recipe | | |
|---|---|---|---|---|
| *TG System* | | | | |
| | | Monomer 2" (200 mg/mL) | Monomer 1 (200 mL/mL) | H$_2$O |
| Cleavable tetra-gel | 1$^{st}$ Gel for TG-based iExM | 2 parts | 1 part | 3 parts |
| *PAA System* | | | | |
| | | Acrylamide | Sodium acrylate | Cross-linker | PBS | NaCl |
| BAC-crosslinked expanding gel | 1$^{st}$ Gel for PAA-based iExM | 2.5% | 7.5% | 0.2% BAC | 1x | 2M |
| BAC-crosslinked non-expanding gel | 2$^{nd}$ Gel | 10% | 0 | 0.2% BAC | 0 | 0 |
| DATD-crosslinked expanding gel | 3$^{rd}$ Gel | 2.5% | 7.5% | 0.5% DATD | 1x | 2M |
| DATD-crosslinked non-expanding gel | 4$^{th}$ Gel | 10% | 0 | 0.5% DATD | 0 | 0 |

TABLE 2-continued

Recipes of hydrogel gelling solutions.

| Bis-crosslinked expanding gel | 5$^{th}$ Gel | 2.5% | 7.5% | 0.15% bis | 1x | 2M |

Results and Discussion

To test if the synthesized monomers form hydrogels, we first mixed a stoichiometrically equal amount of monomer 1 and monomer 2 (or 2 or 2") and casted the monomer solution to a circular mold (as discussed above). It was found that, the monomer mixtures indeed formed hydrogels that are optically transparent and mechanically elastic after a 1- to-2-hour incubation at 37° C. To track the overall shapes and sizes of the gels, we mixed to the monomer solutions a trace amount of fluorescent dyes, and imaged the gels using fluorescence microscopy. Similar to radically polymerized polyacrylamide/sodium polyacrylate hydrogels (PAAs), TGs swelled substantially after eluting the salt with ample amount of double-distilled water (here and after, water specifically means double-distilled water) (FIG. 4). We found that the linear expansion factor of TGs was in the range of 3.0-3.5, slightly smaller than that of the PAAs.

Next, we tested if biomolecules, such as antibodies and FPs, can be anchored to TGs and physically pulled apart by the swelling polymer networks. As analog to protein retention ExM (proExM), we first infused the cells and tissue slices with a small molecule linker (NHS-azide) so that the residual primary amines of proteins and antibodies can be covalently bound to the polymer chains (as discussed above). We then formed TGs in situ and digested the samples by soaking in proteinase K (proK), the same strong proteolysis used in proExM. We note that the small molecular linker used in our experiment can be replaced by other molecules as long as they bind both the biomolecules of interest and the terminal or side functional groups of the TG networks.

Using this proExM analog, we embedded and expanded with TGs cultured HEK cells, which were fluorescent-labeled by antibodies (FIG. 6). The immunostained microtubules showed <4% RMS error before and after the expansion, comparable to the previously reported value of PAA gels using a similar metrics for the global isotropy (FIG. 6). These results suggest that TGs stay mechanical integrated during the handling and the imposed deformation is comparable to that to the PAAs.

Figures 9A, 9B:
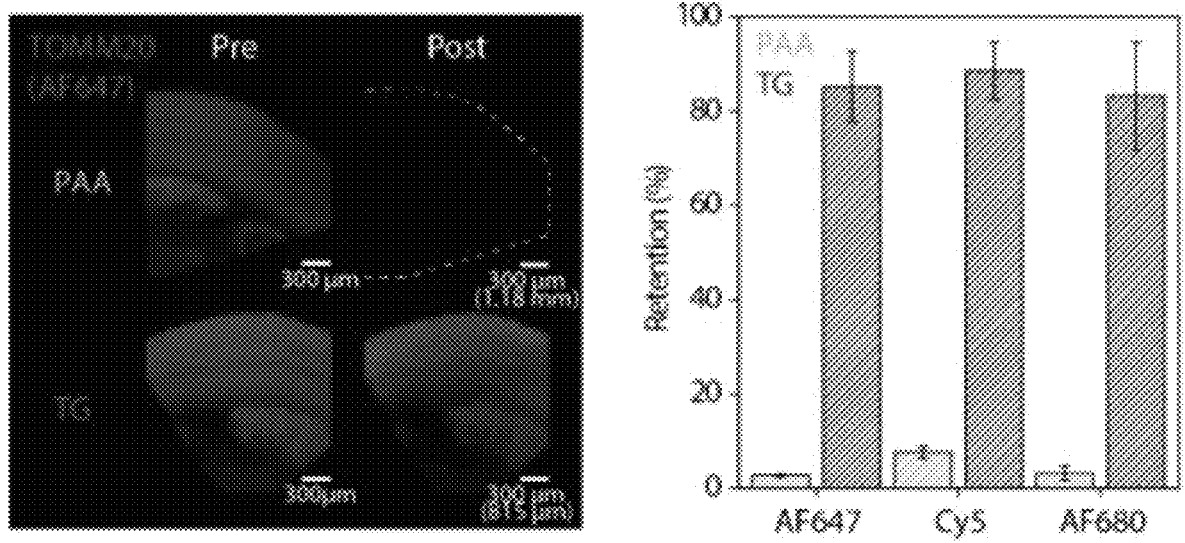
FIG. 9A: Pre-expansion (left column) and post-expansion (right column) Thy1-YFP mouse brain slices immunostained with TOMM20 primary antibodies and AF647-conjugated secondary antibodies, using polyacrylamide/sodium polyacrylate gels (PAAs, top row) and TGs (bottom row). Scale bars, 300 µm (top right, 1.18 mm; bottom right, 815 µm).
FIG. 9B: Fluorescence retention of far-red and infra-red dyes (AF647, Cy5 and AF680) using PAAs and TGs.
Figure 10:
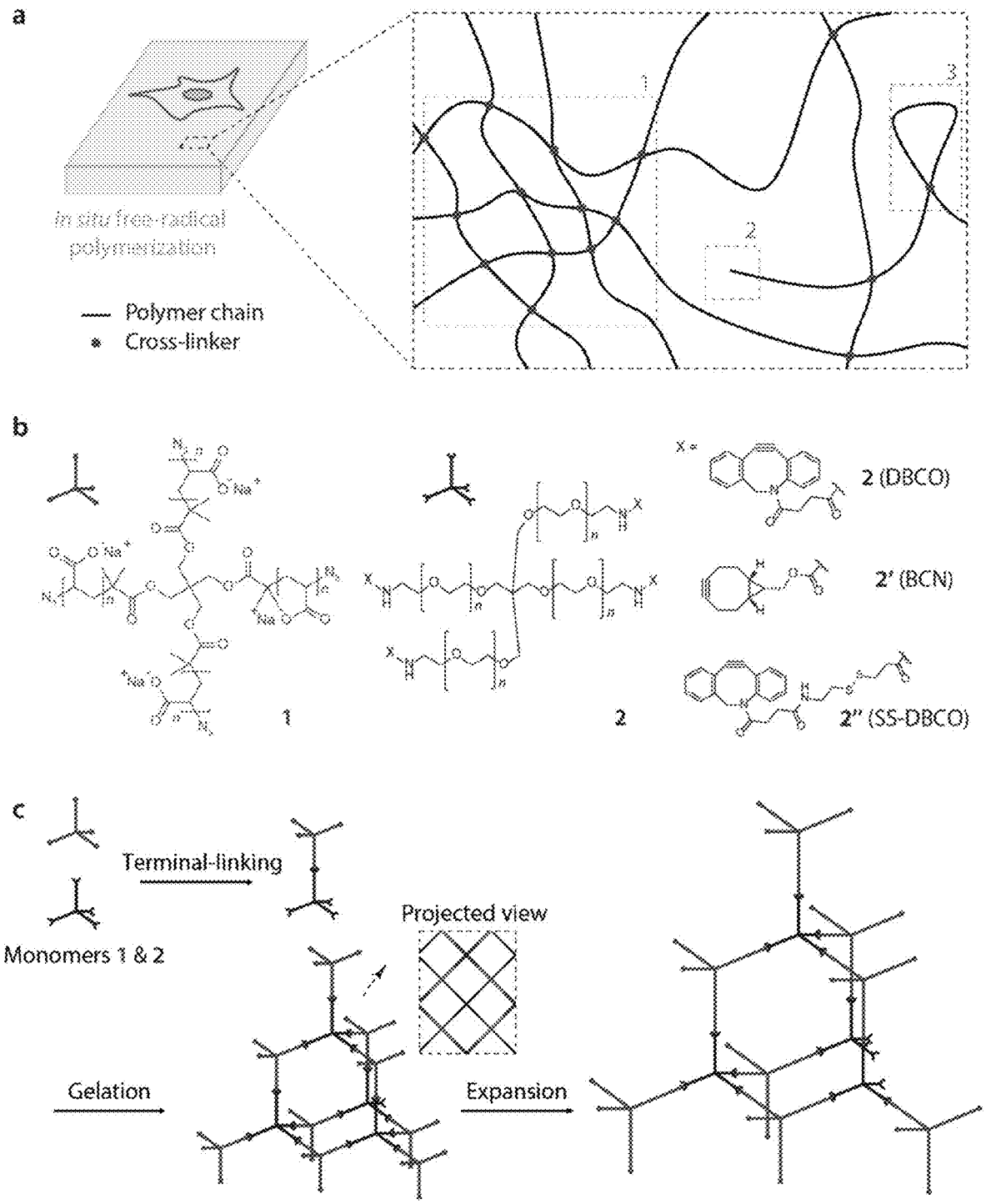
FIG. 10: Design and synthesis of structurally homogenous hydrogel matrix for expansion of nanoscale biological structures. a, Cell/tissue-hydrogel composites formed by in situ free-radical polymerization have structural inhomogeneities at 10-100 nm length scale due to (1) the local fluctuation of monomer and cross-linking density, and (2) the dangling ends and (3) loops in the polymer chains. b, Design of monomers 1 and 2 (monomers A and B; and referred to in the Examples as "monomer 1" and "monomer 2") with tetrahedral symmetry and reactive terminal groups. Modification of monomer 2 terminal groups (2, 2' and 2") allows fine tuning of the reactivity between the monomers and additional functionality of, for example, cleavability. c, Formation and expansion of tetra-gels (TGs) via click chemistry-based terminal-linking of monomers 1 and 2 (or 2', 2"). Inset, projected planar view of the polymerized network.

In addition to the cultured cells, we were also able to embed and expand with TGs thinly-sectioned mouse brain slices, which were fluorescent-labeled by endogenously expressed fluorescent proteins and subsequent post-expansion immunostaining (FIG. 5A). We found that TGs had better preserved dye molecules that were susceptible to free radicals, such as the cyanine dyes (FIG. 9). The drastically increased fluorescence retention of red and far-red dyes demonstrates one of the advantages to move away from the radical polymerization to better preserve both exogenous and endogenous molecules (FIG. 9).

Finally, we used HSV-1 virions to evaluate the nanoscopic isotropy of TGs. This is because that HSV-1 virions had (a) well-defined layered protein structures that had been extensively characterized by conventional high-resolution imaging methods such as electron microscopy (EM) and super-resolution microscopy, (b) the right size to validate the local isotropy at ~10-100 nm length scale, and (c) established purification and immobilization methods there were easily accessible to us.

Figures 11A, 11B, 11C, 11D:
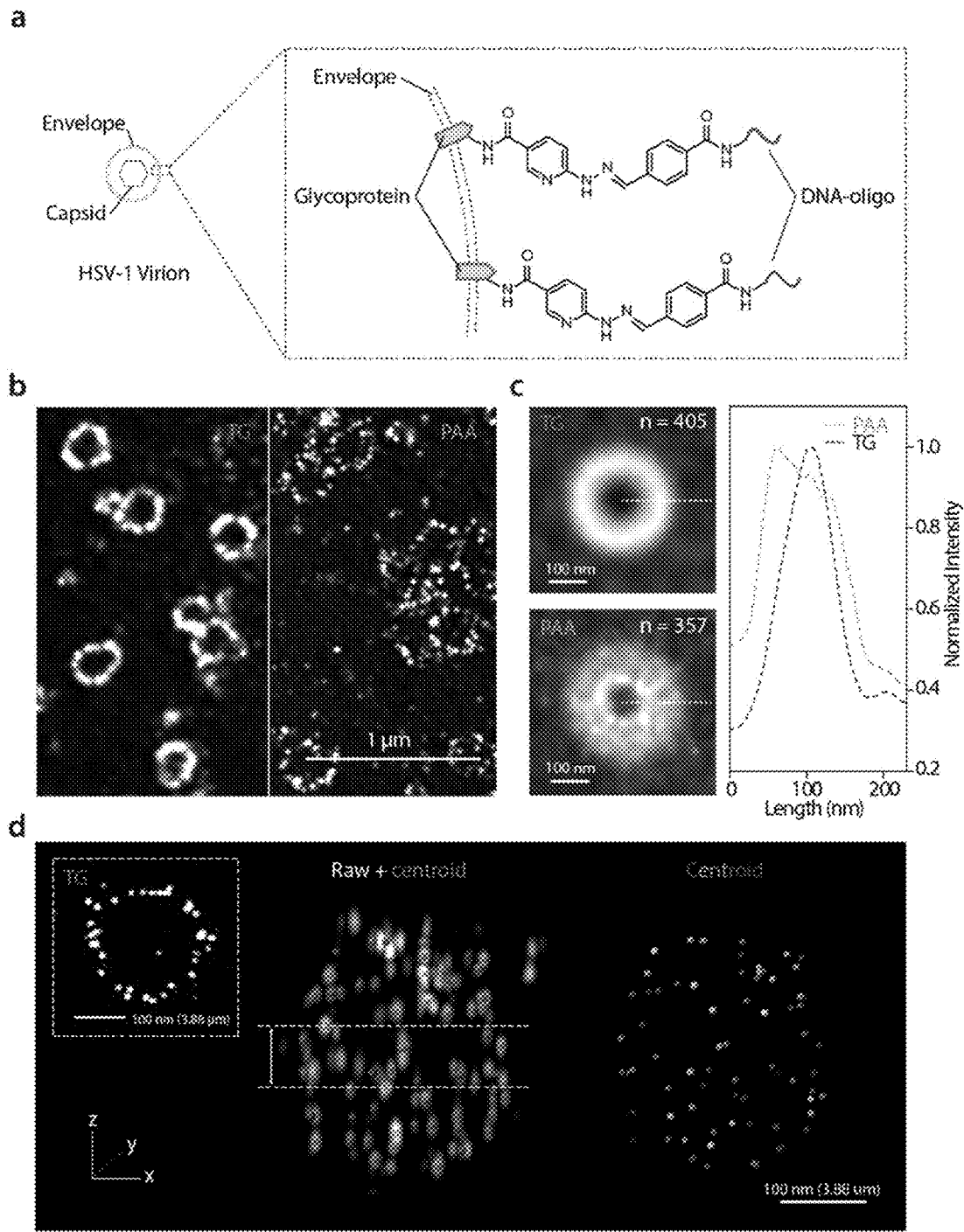
FIG. 11A-11D: Tetragel (TG)-based iterative expansion enables nanoscopically isotropic expansion at 10-100 nm length scale. a, Short DNA-oligos (22 base pairs) were directly anchored to the envelope proteins of an HSV-1 virion via hydrazone formation. The DNA-oligos were used for signal transferring, amplification, and fluorescence readout in the subsequent iterative expansion process. b, HSV-1 virions with oligo-labeled envelope proteins, expanded by TG-based (left) and PAA-based (right) two-round iterative expansion. Scale bar, 1 µm (10.3 µm and 15.3 µm for TG and PAA, respectively). c, Left, averaged single-particle images of HSV-1 virions by TG-based (top) and PAA-based (bottom) expansion. Scale bars, 100 nm. Right, normalized fluorescence intensity along the dotted lines. d, 3D rendered images of an HSV-1 virion particle with the oligo-labeled envelope proteins, expanded by TG-based three-round iterative expansion. The raw data (white, left) overlaid with the fitted centroids (red, left) and the extracted centroids (colored, right) are shown. Scale bars, 100 nm (3.83 µm). Inset, maximum intensity projection (MIP) of the same virion particle over a ~65 nm range close to the particle center (as shown between the two lines in the rendered image). Scale bars, 100 nm (3.83 µm).

Before expansion, we directly conjugated short DNA-oligos to the HSV-1 envelope proteins (diameter=~50-300 nm, width=~50 nm) for the subsequent labeling transfer and fluorescence read-outs. With this new direct-labeling strategy, we were able to achieve a high-density labeling on the virion surface with significantly reduced size compared with that used in iExM, which was a combination of primary antibodies and oligo-conjugated secondary antibodies (FIG. 11). The HSV-1 virions were first iteratively expanded for two rounds (FIG. 11) using the TG-based (1st round: TG; 2nd and 3rd round: PAA; TG-iExM) or PAA-based (1st round: PAA; 2nd and 3rd round: PAA; PAA-iExM) iterative expansion process.

Figure 12:
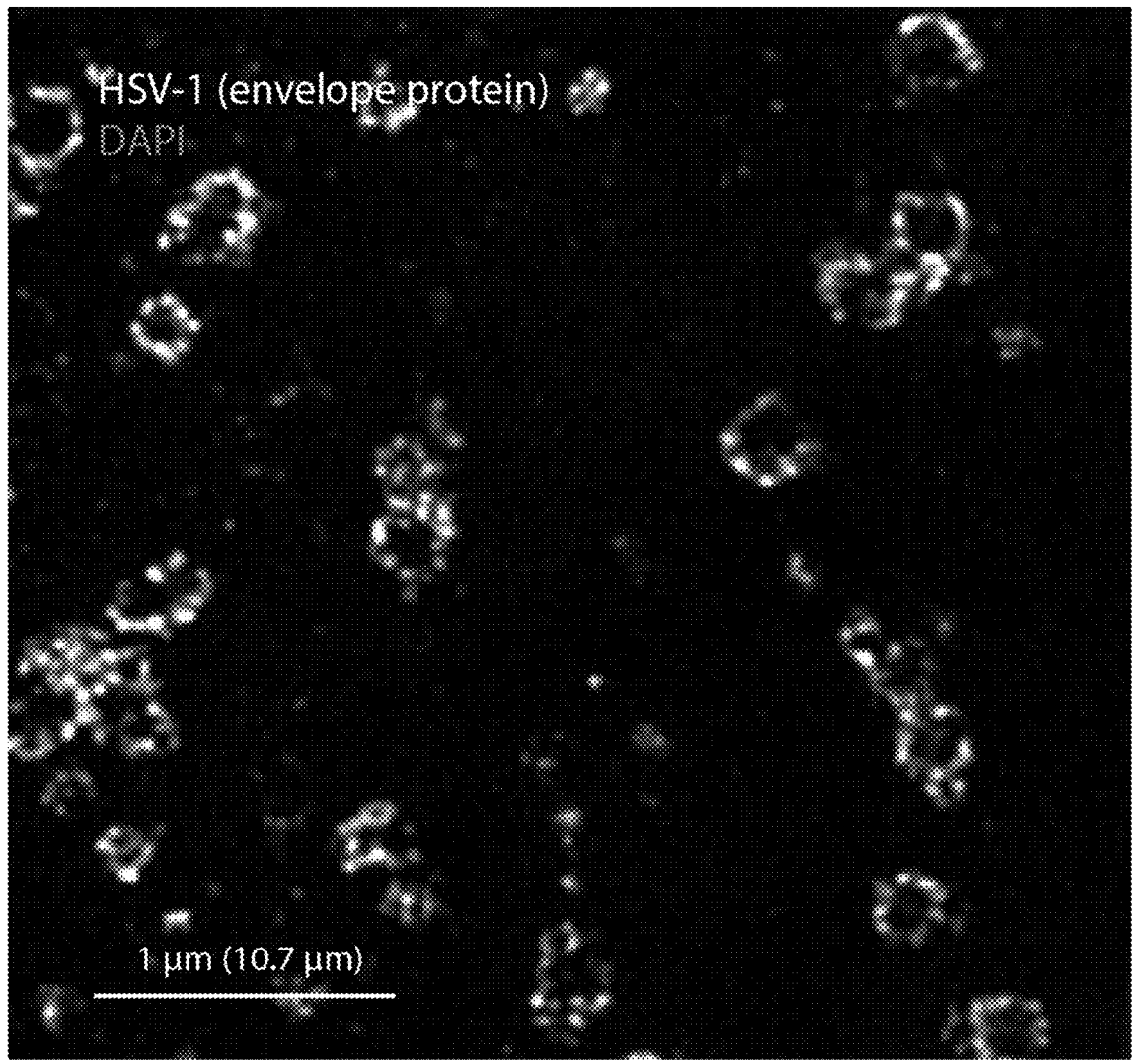
FIG. 12: HSV-1 virions with oligo-labeled envelope proteins (white) and DAPI-labeled DNAs (blue). The virions were expanded by TG-based 10-fold iterative expansion. Scale bar, 1 µm (10.7 µm).

As result, the TG-expanded virion particles showed continuous envelopes with significantly higher labeling density and signal-to-background ratio, compared with the PAA-expanded virion particles. To validate the local isotropy of the expansion at 10-100 nm length scale, we compared the widths of the virion envelope by generating an averaged single virion particle image from over 350 virion particles (FIG. 11). We found that the FWHM of the averaged virion envelope width was 74.5 nm (n=405) and 115.0 nm (n=357) for TG-iExM and PAA-iExM, respectively. In addition, we found that the mean diameter of the expanded virions expansion was 193.1 nm (n=429) and 210.9 nm (n=395) for TG-iExM and PAA-iExM, respectively (P<0.0001). TG-iExM showed a virion diameter closer to the previously reported value using STORM. We also note that by applying the DAPI staining post-expansion, we were able to simultaneously visualize the envelope proteins and DNAs of the HSV-1 virions (FIG. 12).

Finally, we applied 3-round TG-based iterative expansion to the HSV-1 virions, which yielded a 38~40-fold expanded virion with an effective lateral resolution of ~7 nm (=Abbe's diffraction limit/40=640/(2*1.15)/40=6.96 nm) and axial resolution of ~20 nm (=axial length of the confocal PSFs/40=~800 nm/40=~20 nm) (FIG. 11). We note that there are a few factors that could contribute to the sparsity of the surface protein labeling: (a) labeling density at pre-expansion state, (b) mesh size of the TG networks, and (c) loss of labeling during the iterative process. Future investigation awaits to address these issues to achieve high labeling density for high-order expansion.

In ExM, biomolecules and fluorescent tags are anchored to a swellable hydrogel, and then pulled apart by the expanding polymer networks. Recently, multiple variants of ExM have been developed to retain proteins and RNAs in the specimen [proExM, UW version of proExM, ExFISH, ExPath, MAP, and U-ExM], and to achieve higher effective resolution by applying the expansion process iteratively [iExM] or switching to a highly swellable hydrogel [DMAA]. However, as discussed above, these ExM variants suffer from nanoscopic structural inhomogeneities introduced by free-radical polymerization which imposes an intrinsic limitation on the local expansion isotropy at 10-100 nm length scale. Here we show a new class of swellable hydrogels that are tailored to overcome the local density fluctuations of monomers and cross-linkers and the topological defects introduced by radical polymerization. By design, the polymer chain length and the cross-linking density of TGs are uniform throughout the gel, due to the uniform monomer size and the complementary, self-limiting polymerization mechanism between the two types of the monomers. In addition, loops and dangling ends, typical for radical polymerization, are substantially reduced due to the highly specific and stochiometric terminal linking of the monomers. Formed by click-chemistry based terminal-linking of tetrahedral monomers, and termed as tetra-gels, these non-radically polymerized hydrogels swell in water and expand cell and tissue samples up to 3~3.5-fold. Combining the tetra-gel-based iterative expansion and a direct-labeling strategy of virion envelop proteins, we have expanded HSV-1 virions 10- and 40-fold with two or three rounds of expansions, respectively. We have found that the tetra-gel-expanded virions have ~0.6 times smaller envelope widths compared with those expanded with polyacrylamide/polyacrylate hydrogels, validating that the tetra-gels are able to capture 10-100 nm biological structures with superior local isotropy. Our approach and finding serve as a guiding principle for materials design to realize ideal expansion of biological structures and open up potential applications in fields such as structural biology.

REFERENCES

1. Chen, F., Tillberg, P. W. & Boyden, E. S. Optical imaging. Expansion microscopy. *Science* 347, 543-548, doi: 10.1126/science.1260088 (2015).
2. Chen, F. et al. Nanoscale imaging of RNA with expansion microscopy. *Nat Methods* 13, 679-684, doi: 10.1038/nmeth.3899 (2016).
3. Tillberg, P. W. et al. Protein-retention expansion microscopy of cells and tissues labeled using standard fluorescent proteins and antibodies. *Nat Biotechnol* 34, 987-992, doi: 10.1038/nbt.3625 (2016).
4. Chang, J. B. et al. Iterative expansion microscopy. *Nat Methods*, doi: 10.1038/nmeth.4261 (2017).
5. Di Lorenzo, F. & Seiffert, S. Nanostructural heterogeneity in polymer networks and gels. *Polym Chem-Uk* 6, 5515-5528, doi: 10.1039/c4py01677g (2015).
6. Orakdogen, N. & Okay, O. Correlation between cross-linking efficiency and spatial inhomogeneity in poly(acrylamide) hydrogels. *Polym Bull* 57, 631-641, doi: 10.1007/s00289-006-0624-1 (2006).
7. Yazici, I. & Okay, O. Spatial inhomogeneity in poly (acrylic acid) hydrogels. *Polymer* 46, 2595-2602, doi: 10.1016/j.polymer.2005.01.079 (2005).
8. Sakai, T. et al. Design and fabrication of a high-strength hydrogel with ideally homogeneous network structure from tetrahedron-like macromonomers. *Macromolecules* 41, 5379-5384, doi:10.1021/ma800476x (2008).
9. Oshima, K., Fujimoto, T., Minami, E. & Mitsukami, Y. Model Polyelectrolyte Gels Synthesized by End-Linking of Tetra-Arm Polymers with Click Chemistry: Synthesis and Mechanical Properties. *Macromolecules* 47, 7573-7580, doi:10.1021/ma501786h (2014).

While this invention has been particularly shown and described with references to preferred embodiments thereof, it will be understood by those skilled in the art that various changes in form and details may be made therein without departing from the scope of the invention encompassed by the appended claims.

What is claimed is:

1. A hydrogel that is the product of a non-radical polymerization reaction between a monomer of Formula (A1):

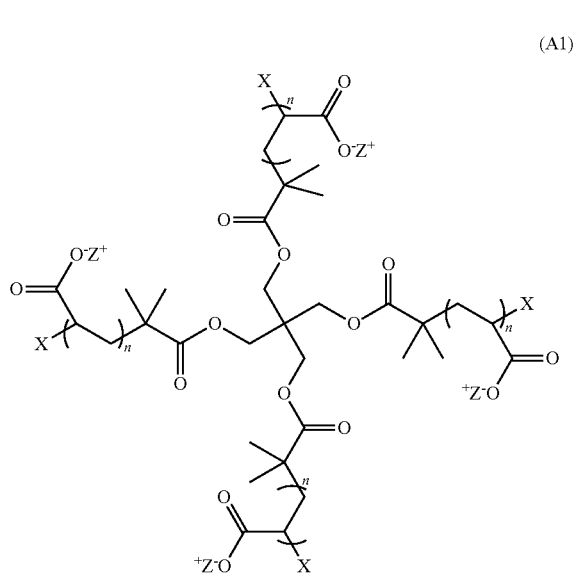

and a monomer of Formula (B1):

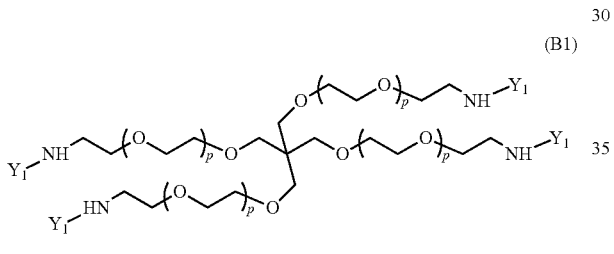

wherein:
  each n is an integer greater than or equal to 1;
  each p is an integer greater than or equal to 1;
  $Z^+$ is a counter cation;
  X and $Y_1$ are each crosslinkable moieties, and
  X and $Y_1$ covalently crosslink to end-link the monomers.

2. The hydrogel of claim 1, wherein X is a moiety comprising a terminal azide group and $Y_1$ is a moiety comprising a terminal alkyne, and wherein X and $Y_1$ crosslink by copper-free azide-alkyne cycloaddition.

3. The hydrogel of claim 1, wherein X and $Y_1$ crosslink by amine-NHS ester reaction.

4. The hydrogel of claim 1, wherein X and $Y_1$ crosslink by maleimide-thiol reaction.

5. The hydrogel of claim 1, wherein X and $Y_1$ crosslink by trans-cyclooctene (TCO)-tetrazine reaction.

6. The hydrogel of claim 1, wherein the hydrogel is labelled.

7. A composite comprising a biological sample and the hydrogel of claim 1.

8. A method of preparing the composite of claim 7, comprising permeating the biological sample with a monomer of Formula (A1) or a monomer of Formula (A3), and a monomer of Formula (B1) to form a hydrogel by non-radical polymerization.

9. A method of microscopy comprising:
  a. permeating the biological sample with a monomer of Formula (A1):

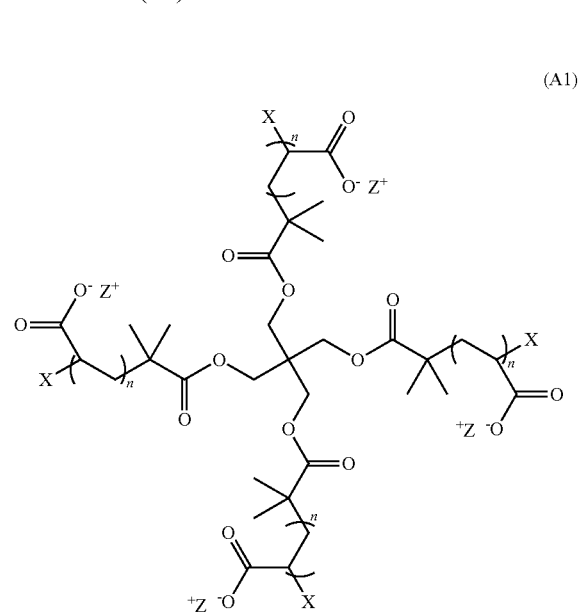

and a monomer of Formula (B1):

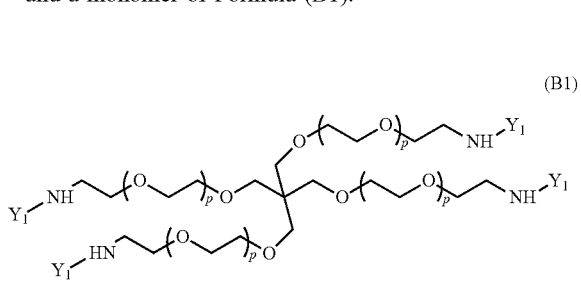

to form a hydrogel according to claim 1 by non-radical polymerization;

b. isotropically expanding the composite by contacting it with an aqueous solution; and c. viewing the expanded composite using microscopy;

wherein:
  each n is an integer greater than or equal to 1;
  each p is an integer greater than or equal to 1;
  $Z^+$ is a counter cation
  X and $Y_1$ are each crosslinkable moieties, and
  X and $Y_1$ covalently crosslink to end-link the monomers.

10. A method for in-situ sequencing of target nucleic acids present in a biological sample comprising the steps of:
  a. attaching target nucleic acids present in the sample with a molecule linker or nucleic acid adapter;

b. permeating the sample with a monomer of Formula (A1):

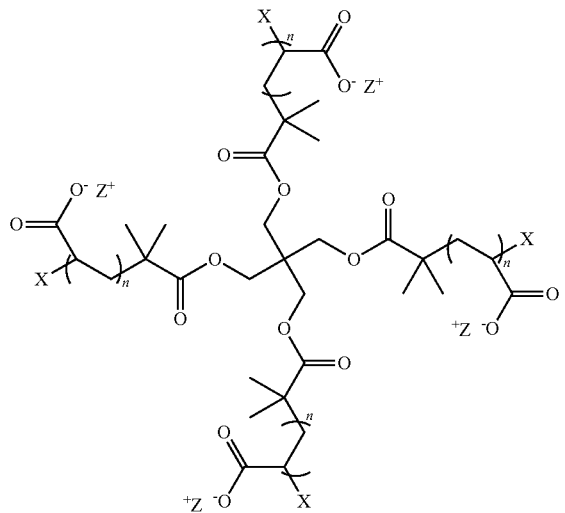

and a monomer of Formula (B1):

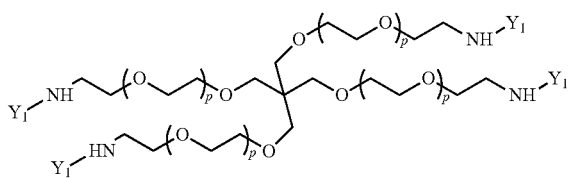

to form a hydrogel according to claim 1 by non-radical polymerization and thereby forming a sample-hydrogel complex, wherein the small molecule linker or nucleic acid adaptor is attached both to the target nucleic acids present in the sample and to the hydrogel;

c. digesting proteins present in the sample;
d. expanding the complex to form a first enlarged sample;
e. re-embedding the first enlarged sample in a non-swellable material to form a re-embedded complex;
f. modifying the target nucleic acids or the nucleic acid adaptor to form a target nucleic acids or a nucleic acid adaptor; and
g. sequencing the nucleic acids present in the re-embedded complex;

wherein:
each n is an integer greater than or equal to 1;
each p is an integer greater than or equal to 1;
$Z^+$ is a counter cation;
X and $Y_1$ are each crosslinkable moieties, and
X and $Y_1$ covalently crosslink to end-link the monomers.

11. A method for enlarging a biological sample for microscopy, the method comprising the steps of:
a) permeating a sample with a first hydrogel, wherein the sample is anchored to the swellable material;
b) swelling the swellable material resulting in a first expanded sample;
c) optionally permeating the first expanded sample with a second hydrogel; and
d) optionally swelling the second hydrogel resulting in a second expanded sample;
wherein the first hydrogel and/or the second hydrogel is the hydrogel of claim 1.

* * * * *

UNITED STATES PATENT AND TRADEMARK OFFICE
CERTIFICATE OF CORRECTION

PATENT NO. : 11,873,374 B2
APPLICATION NO. : 16/267849
DATED : January 16, 2024
INVENTOR(S) : Gao et al.

Page 1 of 1

It is certified that error appears in the above-identified patent and that said Letters Patent is hereby corrected as shown below:

In the Specification

In Column 1, Lines 10-13, delete:
"This invention was made with government support under Grant No. 6936173 awarded by ARO and under Grant No. 6934416 awarded by the National Institutes of Health. The government has certain rights in the invention."

And insert:
-- This invention was made with government support under HG008525 and R01 DA029639 awarded by the National Institutes of Health, W911NF-15-1-0548 awarded by the U.S. Army Research Office, and DUE1734870 awarded by the National Science Foundation. The government has certain rights in the invention. --

Signed and Sealed this
Fourth Day of November, 2025

John A. Squires
*Director of the United States Patent and Trademark Office*